US009575074B2

(12) United States Patent
Sakamoto et al.

(10) Patent No.: US 9,575,074 B2
(45) Date of Patent: Feb. 21, 2017

(54) METHOD FOR EVALUATING ATHEROSCLEROTIC LESION, AND KIT

(71) Applicants: Hitachi, Ltd., Chiyoda-ku, Tokyo (JP); National University Corporation Hokkaido University, Sapporo-shi, Hokkaido (JP)

(72) Inventors: Takeshi Sakamoto, Asaka (JP); Hiroko Hanzawa, Tokorozawa (JP); Naomi Manri, Kawagoe (JP); Yuji Kuge, Sapporo (JP)

(73) Assignees: Hitachi, Ltd., Tokyo (JP); National University Corporation Hokkaido University, Sapporo-shi (JP)

( * ) Notice: Subject to any disclaimer, the term of this patent is extended or adjusted under 35 U.S.C. 154(b) by 0 days.

(21) Appl. No.: 14/935,994

(22) Filed: Nov. 9, 2015

(65) Prior Publication Data

US 2016/0061846 A1    Mar. 3, 2016

Related U.S. Application Data

(62) Division of application No. 13/885,921, filed as application No. PCT/JP2011/076499 on Nov. 17, 2011, now abandoned.

(30) Foreign Application Priority Data

Nov. 17, 2010    (JP) ................. 2010-257065

(51) Int. Cl.
| | | |
|---|---|---|
| *G01N 31/00* | (2006.01) | |
| *G01N 33/53* | (2006.01) | |
| *G01N 33/68* | (2006.01) | |
| *A61B 5/02* | (2006.01) | |
| *A61B 5/055* | (2006.01) | |
| *A61B 5/00* | (2006.01) | |
| *A61B 6/00* | (2006.01) | |
| *A61B 8/08* | (2006.01) | |

(52) U.S. Cl.
CPC ....... *G01N 33/6893* (2013.01); *A61B 5/02007* (2013.01); *A61B 5/055* (2013.01); *A61B 6/508* (2013.01); *A61B 5/0071* (2013.01); *A61B 6/504* (2013.01); *A61B 8/0891* (2013.01); *G01N 2800/323* (2013.01); *G01N 2800/52* (2013.01)

(58) Field of Classification Search
CPC ............ G01N 33/6893; G01N 2800/52; G01N 2800/323; G01B 5/012; G01B 7/002; B23Q 3/1554; B23Q 3/15526
See application file for complete search history.

(56) References Cited

U.S. PATENT DOCUMENTS

| | | |
|---|---|---|
| 4,444,879 A | 4/1984 | Foster et al. |
| 8,603,829 B2 | 12/2013 | Kuge et al. |

FOREIGN PATENT DOCUMENTS

| | | |
|---|---|---|
| JP | 2007-278907 A | 10/2007 |
| JP | 2010-85242 A | 4/2010 |
| JP | 2011-58949 A | 3/2011 |
| JP | 2011-232218 A | 11/2011 |
| JP | 2012-107989 A | 6/2012 |
| JP | 2012-108150 A | 6/2012 |

OTHER PUBLICATIONS

Kang et al. (Journal of Proteome Research, 2010, vol. 9, pp. 1157-1164).*
Frolova et al., (Circ Res. Nov. 26, 2010;107(11):1313-25. doi: 10.1161/CIRCRESAHA.110.232371. Epub Sep. 30, 2010).*
Fach et al. (Molecular & Cellular Proteomics vol. 3, pp. 1200-1210, 2004).*
A. E. Canfield et al., "The Involvement of Matrix Glycoproteins in Vascular Calcification and Fibrosis: an Immunohistochemical Study", Journal of Pathology, 2002, pp. 228-234, vol. 196.
A. Stroem et al., "Extracellular Matrix Components in Atherosclerotic Arteries of Apo E/LDL Receptor Deficient Mice: An Immunohistochemical Study", Histology and Histopathology, Cellular and Molecular Biology, 2004, pp. 337-347, vol. 19.
Sam Hanash, "Disease Proteomics", Nature, Mar. 13, 2003, pp. 226-232, vol. 422.
Japanese-language Written Opinion (PCT/ISA/237) dated Feb. 28, 2013 (Four (4) pages).
International Search Report dated Feb. 28, 2013 with English Translation (Five (5) pages).
Frolova et al., (Circ. Res Nov. 26, 2010; 107(11):1313-25. doi: 10.1161/CIRCRESAHA.110.232371. Epub Sep. 30, 2010).
Kang et al. Molecular proteomics imaging of tumor interfaces by mass spectrometry. Journal of Proteome Research, vol. 9, pp. 1157-1164, 2010, published online Oct. 12, 2009.

* cited by examiner

*Primary Examiner* — Lisa Cook
(74) *Attorney, Agent, or Firm* — Crowell & Moring LLP

(57) ABSTRACT

The present invention provides a method and a means for evaluating atherosclerotic lesions by identifying a protein (marker protein) group, the expression level of which varies according to the progression of the atherosclerotic lesion, and using the proteins. Specifically, the present invention relates to a method for evaluating atherosclerotic lesions, comprising the steps of detecting a marker protein exhibiting an expression pattern (expression variation) characteristic at a specific disease stage of atherosclerotic lesions in a subject, and evaluating the atherosclerotic lesions in the subject based on the detection result.

5 Claims, 8 Drawing Sheets

Fig. 8
Plastin-2
Intermediate lesion | Late lesion
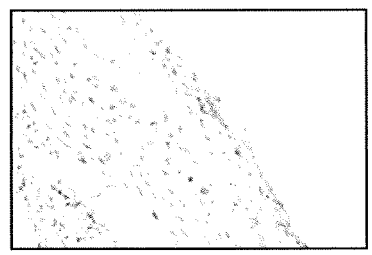 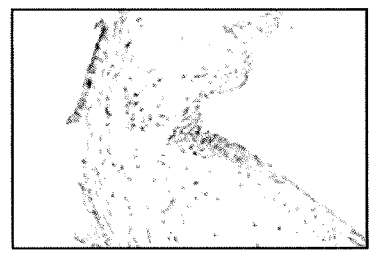
Tenascin
Intermediate lesion | Late lesion
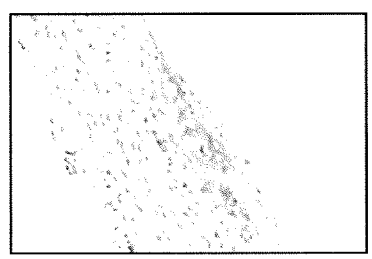 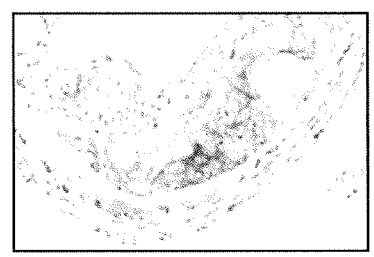

METHOD FOR EVALUATING ATHEROSCLEROTIC LESION, AND KIT

CROSS REFERENCE TO RELATED APPLICATIONS

This application is a divisional of U.S. application Ser. No. 13/885,921, filed May 16, 2013, which is a National Stage of PCT International Application No. PCT/JP2011/076499, filed Nov. 17, 2011, which claims priority from Japanese Patent Application No. 2010-257065, filed on Nov. 17, 2010, the disclosures of which are expressly incorporated by reference herein.

TECHNICAL FIELD

The present invention relates to a method, a kit, and an apparatus for evaluating atherosclerotic lesions. More specifically, the present invention relates to a method, a kit, and an apparatus for evaluating atherosclerotic lesions based on novel marker protein(s). Furthermore, the present invention relates to agent(s) for visualizing atherosclerotic lesions and agent(s) for targeting atherosclerotic lesions using the marker protein(s), and a method for evaluating the effectiveness of the therapeutic agent(s) or therapeutic method(s) for atherosclerotic lesions.

BACKGROUND ART

Arteriosclerosis proceeds over a long period of time without subjective symptoms, and induces cardiac diseases such as severe myocardial infarction or cerebrovascular diseases such as cerebral infarction or cerebral hemorrhage. Arteriosclerosis progresses to result in the formation of atherosclerotic lesions (atheroma or plaque) within arterial blood vessels. Plaques include stable plaques rich in calcified fibrous tissue and unstable plaques rich in lipids or inflammatory cells, in which fibrous caps are thinned. Most acute atherosclerotic diseases such as myocardial infarction and brain infarction are induced by rupture of unstable plaques and thrombus formation. Therefore, it is important to appropriately evaluate and diagnose the formation and growth conditions of unstable plaques and the rupture risk thereof in acute atherosclerotic diseases. Arteriosclerosis is currently detected mainly by angiography, which involves evaluation of the degree of stenosis, but it is problematic because information concerning intravascular plaque formation or the properties thereof can barely be obtained. Moreover, angiography is highly invasive. Hence, a low-invasive method for detecting atherosclerotic lesions has been required.

Disease proteomics is a technique for exhaustively searching increases or decreases in protein levels that vary depending on specific diseases when compared with a healthy state, using a body fluid such as blood, saliva, or urine, or a tissue sample, as a material. Disease proteomics is a technique characterized by enabling simultaneous extraction and/or detection of a plurality of factors, the association of which with diseases is conventionally unknown. Application of multiple specimens to and increased sensitivity for a 2D electrophoresis method and measuring apparatuses such as protein microarrays and mass spectrometry have been realized. Thus, data analysis technology has been in place and is applied in searches for markers for various diseases including cancer, immunity disorders, infections, and the like (Non-patent document 1).

For example, methods for diagnosing arteriosclerosis or diseases associated therewith by using biochemical markers have been reported, wherein the blood levels of the biochemical markers vary as atherosclerotic lesions develop, (patent documents 1 and 2). However, further development of marker groups is desired in order to precisely diagnose atherosclerotic lesions.

CITATION LIST

Patent Documents

Patent Document 1: JP Patent Publication (Kokai) No. 2007-278907 A
Patent document 2: JP Patent Publication (Kokai) No. 2010-85242 A

Non-Patent Documents

Non-patent document 1: Hanash S., Nature, vol. 422, pp. 226-232, 2003

SUMMARY OF THE INVENTION

Problem to be Solved by the Invention

Formation of atherosclerotic lesions, and unstable lesions in particular, induces severe diseases such as myocardial infarction and brain infarction. Hence, precise diagnosis thereof is an important issue. If precise evaluation of unstable arteriosclerotic lesions becomes possible, this would enable prevention of a disease through improvement of lifestyle or the like, prevention of progression and/or worsening of the disease, and treatment of the disease.

Therefore, an object of the present invention is to provide diagnosis, prevention, or evaluation for treatment of atherosclerotic lesions by identifying protein groups (maker proteins, the expression levels of which vary with the progression of atherosclerotic lesions) with a proteomic technique, recording the variations in an expression profile database, comparing the data with the variations in the expression levels of marker proteins in samples obtained from subjects, and thereby identifying the stage of progression of atherosclerotic lesion(s).

Another object of the present invention is to provide a method for evaluating atherosclerotic lesions, comprising:

administering (e.g., via intravenous administration) to a subject a substance having specific affinity for a marker protein group, the expression of which varies with the progression of atherosclerotic lesions, wherein the substance is labeled in advance;

detecting the affinity substance binding to the marker protein in vivo in the subject; and measuring the level of the affinity substance binding to the marker protein.

Means for Solving the Problem

The present inventors have obtained arterial tissue from ApoE-deficient mice, in which arteriosclerosis commonly occurs and progresses at an accelerated rate with administration of a high-fat diet and aging (age in weeks), and wild-type mice. They then exhaustively compared and analyzed the expression levels of proteins contained in the arterial tissue with a mass spectroscope. An expression profile database was constructed using the ratios of the measured expression levels of proteins contained in arterial tissue samples obtained at each age in weeks (12-week-old, 18-week-old, 25-week-old, and 35-week-old) and differing in the extent of the progression of arteriosclerosis. It was discovered that the onset or the progression (worsening) of arteriosclerosis correlates with the variation tendency for each protein expression (level) ratio, and the tendencies can be classified into a plurality of groups. Furthermore, the present inventors have succeeded in identifying proteins that exhibit expression tendencies characteristic of specific stages of arteriosclerotic lesions, and have found that the proteins can be used as markers for evaluation of the likelihood of the onset of arteriosclerosis, high or low risk of contraction of the disease, and possibility of progression, thereby completing the present invention.

The present invention provides the following [1] to [39].

[1] A kit for evaluating an atherosclerotic lesion, comprising at least one type of substance specifically binding to at least one type of protein selected from at least group (a) from among proteins in the following groups (a) to (d):
(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1;
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4.

[2] The kit according to [1], comprising at least two types of substance specifically binding to a protein selected from group (a) and a protein selected from at least one of groups (b) to (d).

[3] The kit according to [1], comprising at least three types of substance specifically binding to a protein selected from group (a) and proteins selected from at least two of groups (b) to (d).

[4] The kit according to [1], comprising at least four types of substance specifically binding to a protein selected from group (a) and proteins selected from each of groups (b) to (d).

[5] A kit for evaluating an atherosclerotic lesion at the intermediate stage or later, comprising at least one type of substance specifically binding to at least one type of protein selected from the group consisting of cartilage oligomeric matrix protein, fibromodulin, fibronectin, and thrombospondin-4.

[6] A kit for evaluating an atherosclerotic lesion at the initial or the intermediate stage, comprising at least one type of substance specifically binding to at least one type of protein selected from the group consisting of plastin-2, tenascin, CD5 antigen-like protein, properdin, Cb4-binding protein, fibrinogen beta chain, and fibrinogen gamma chain.

[7] A kit for evaluating an atherosclerotic lesion at the late stage, comprising at least one type of substance specifically binding to at least one type of protein selected from the group consisting of vitronectin, matrix metalloproteinase-2, and thrombospondin-1.

[8] The kit according to any one of [1] to [7], the evaluation of an atherosclerotic lesion is selected from the group consisting of the determination of the presence of an atherosclerotic lesion in a subject, the determination of the stage of an atherosclerotic lesion in a subject, the determination of the location of an atherosclerotic lesion in a subject, the evaluation of the therapeutic effect of arteriosclerosis existing in a subject, and the prediction of prognosis of arteriosclerosis existing in a subject.

[9] The kit according to any one of [1] to [8], wherein a substance specifically binding to a protein is selected from the group consisting of an antibody, an antibody-like molecule, a nucleic acid aptamer, a ligand, and a substrate.

[10] The kit according to any one of [1] to [9], wherein the substance specifically binding to a protein is bound to a contrast medium.

[11] The kit according to [10], wherein the contrast medium is selected from the group consisting of a fluorescent substance, a luminescent substance, a radioactive substance, a liposome, a micelle, a cell, a virus particle, a virus, a microparticle, a nanoparticle, a microdevice with a space, an emulsion, a lipid disc, a polymer, a gadolinium-conjugated molecule, a superparamagnetic iron oxide particle, a perfluorocarbon nanoparticle, and an ultrafine bubble.

[12] The kit according to [10] or [11], wherein the atherosclerotic lesion is visualized by a means selected from the group consisting of positron emission tomography (PET), single photon emission computed tomography (SPECT), γ scintigraphy, autoradiography, fluorescent imaging, magnetic resonance imaging (MRI), ultrasonication, and computed tomography (CT).

[13] An apparatus for evaluating an atherosclerotic lesion, comprising:
(i) a means of detecting at least one type of protein selected from at least group (a) from among proteins shown in the following groups (a) to (d), in a subject:
(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4; and
(ii) a means of evaluating the atherosclerotic lesion in the subject based on the detection results obtained by means (i).

[14] The apparatus according to [13], further comprising:
(iii) a means of storing the standard levels of the above proteins; and
(iv) a means of comparing the protein detection results in the subject with the standard levels.

[15] An agent for visualizing an atherosclerotic lesion, comprising at least one type of protein selected from at least group (a) from among proteins in the following groups (a) to (d), and a contrast medium binding thereto:

(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4.

[16] An agent for visualizing an atherosclerotic lesion at the intermediate stage or later, comprising:
  at least one type of substance specifically binding to at least one type of protein selected from the group consisting of cartilage oligomeric matrix protein, fibromodulin, fibronectin, and thrombospondin-4; and
  a contrast medium binding thereto.

[17] An agent for visualizing an atherosclerotic lesion at the initial or the intermediate stage, comprising:
at least one type of substance specifically binding to at least one type of protein selected from the group consisting of plastin-2, tenascin, CD5 antigen-like protein, properdin, Cb4-binding protein, fibrinogen beta chain, and fibrinogen gamma chain; and a contrast medium binding thereto.

[18] An agent for visualizing an atherosclerotic lesion at the late stage, comprising:
  at least one type of substance specifically binding to at least one type of protein selected from the group consisting of vitronectin, matrix metalloproteinase-2, and thrombospondin-1; and
  a contrast medium binding thereto.

[19] A targeting agent for directing a compound or a molecule to an atherosclerotic lesion, comprising a substance specifically binding to at least one type of protein selected from at least group (a) from among the following groups (a) to (d), and the compound or the molecule binding thereto:
(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4.

[20] The targeting agent according to [19], wherein the compound or the molecule is a thrombolytic agent.

[21] A method for evaluating the effectiveness of a therapeutic agent or a therapeutic method for an atherosclerotic lesion, comprising the steps of:
(i) detecting at least one type of protein selected from at least group (a) from among proteins shown in the following groups (a) to (d) in an animal with an atherosclerotic lesion treated by a test therapeutic agent or a test therapeutic method:
(a) cartilage oligomeric matrix protein, fibromodulin, fibronectin, and thrombospondin-4; (b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4; and
(ii) evaluating the effectiveness of the test therapeutic agent or the test therapeutic method on the atherosclerotic lesion based on the results of (i).

[22] The method according to [21], further comprising a step of detecting the protein in an animal with an atherosclerotic lesion before treatment using the test therapeutic agent or the test therapeutic method.

[23] The method according to [21] or [22], wherein an animal having an atherosclerotic lesion is an arterial disease animal model.

[24] A method for evaluating an atherosclerotic lesion, comprising the steps of:
(i) detecting at least one type of protein in a subject selected from at least group (a) from among proteins shown in the following groups (a) to (d):
(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4; and
(ii) evaluating the atherosclerotic lesion in the subject based on the results of (i).

[25] The method according to [24], wherein a protein selected from group (a), and at least two types of protein selected from at least one of groups (b) to (d), are detected.

[26] The method according to [24], wherein a protein selected from group (a), and at least three types of protein selected from at least two of groups (b) to (d), are detected.
[27] The method according to [24], wherein a protein selected from group (a), and at least four types of protein selected from each of groups (b) to (d), are detected.
[28] A method for evaluating an atherosclerotic lesion, comprising the steps of:
(i) detecting at least one type of protein selected from the group consisting of cartilage oligomeric matrix protein, fibromodulin, fibronectin, and thrombospondin-4 in a subject; and
(ii) evaluating, based on the results of (i), whether or not the subject has an atherosclerotic lesion at the intermediate stage or later.
[29] A method for evaluating an atherosclerotic lesion, comprising the steps of:
(i) detecting at least one type of protein selected from the group consisting of plastin-2, tenascin, CD5 antigen-like protein, properdin, Cb4-binding protein, fibrinogen beta chain, and fibrinogen gamma chain, in a subject; and
(ii) evaluating whether or not the subject has an atherosclerotic lesion at the initial or intermediate stage based on the results of (i).
[30] A method for evaluating an atherosclerotic lesion, comprising the steps of:
(i) detecting at least one type of protein selected from the group consisting of vitronectin, matrix metalloproteinase-2, and thrombospondin-1 in a subject; and
(ii) evaluating whether or not the subject has an atherosclerotic lesion at the late stage based on the results of (i).
[31] The method according to any one of [24] to [30], wherein step (i) is performed by administering a substance specifically binding to a protein to a subject, and then detecting the substance binding to the protein existing in the subject.
[32] The method according to any one of [24] to [30], wherein the step (i) is performed by preparing a subject-derived sample, bringing the sample into contact with a substance specifically binding to a protein, and then detecting binding between the protein and the substance.
[33] The method according to any one of [24] to [32], wherein evaluation of an atherosclerotic lesion is selected from the group consisting of determination of the presence of an atherosclerotic lesion in a subject, determination of the stage of an atherosclerotic lesion existing in a subject, determination of the location of an atherosclerotic lesion existing in a subject, evaluation of the therapeutic effect on arteriosclerosis existing in a subject, and prediction of prognosis of arteriosclerosis existing in a subject.
[34] The method according to [31] or [32], wherein a substance specifically binding to a protein is selected from the group consisting of an antibody, an antibody-like molecule, a nucleic acid aptamer, a ligand, and a substrate.
[35] The method according to any one of [31], [32], and [34], wherein a substance specifically binding to a protein is bound to a contrast medium.
[36] The method according to [35], wherein the contrast medium is selected from the group consisting of a fluorescent substance, a luminescent substance, a radioactive substance, a liposome, a micelle, a cell, a virus particle, a virus, a microparticle, a nanoparticle, a microdevice with a space, an emulsion, a lipid disc, a polymer, a gadolinium-conjugated molecule, a superparamagnetic iron oxide particle, a perfluorocarbon nanoparticle, and an ultrafine bubble.
[37] The method according to [35] or [36], wherein an atherosclerotic lesion is visualized by a means selected from the group consisting of positron emission tomography (PET), single photon emission computed tomography (SPECT), γ scintigraphy, autoradiography, fluorescent imaging, magnetic resonance imaging (MRI), ultrasonication, and computed tomography (CT).
[38] The method according to any one of [24] to [37], wherein the evaluation step (ii) comprises comparing a measured protein level in a healthy subject with a standard level selected from measured protein levels in subjects with arteriosclerosis at known stages.
[39] The method according to [38], wherein the evaluation step (ii) comprises evaluating whether or not the measured protein level in the subject is higher than the standard level.

Effects of the Invention

The present invention enables detection of arteriosclerotic lesions (destabilization) that have been missed by conventional methods in primary care or medical examination and enables assaying the possibility of the occurrence and progression of the resulting disorder. With the use of the present invention, the ratio of the expression level of a protein group existing in a sample from a subject to the expression level of the same in a standard sample and variations in the ratio over time are measured, and then the results are compared with an expression profile database compiled in advance. This makes it possible to evaluate the possibility of the occurrence of arteriosclerosis and the resulting disorder and the possibility of the progression of the symptoms. Furthermore, the present invention can be used for precisely and conveniently testing or analyzing the possibility of the occurrence of arteriosclerotic lesions and the resulting disorder and the possibility of the progression thereof. The present invention can also be used for developing various reagents or remedies, and related apparatuses.

Furthermore, variations in the expression of a marker protein group selected in this study are visualized by a known means of imaging with a substance specifically binding to the protein (e.g., an antibody, an antibody-like substance, a ligand, and a substrate) and a contrast medium (e.g., a fluorescent substance and a radioactive substance). The progression stage can then be evaluated based on the aspect of the expression of the protein group in the relevant lesions (amount, localization, density, or relative distribution). Thus, it becomes possible to use the present invention as an indicator of the possibility of the formation of atherosclerotic lesions, the occurrence of the resulting disorders, and the progression of symptoms. Furthermore, the present invention can be used for precisely and conveniently assessing or analyzing the possibility of the occurrence of arteriosclerosis and the resulting disorder, and the possibility of the progression thereof. The present invention can also be used for developing various reagents or remedies, and related apparatuses.

BRIEF DESCRIPTION OF THE DRAWINGS

In FIG. 6, "*" indicates the intravascular lumen side.

FIG. 8 shows images showing the expression of markers (plastin-2 and tenascin) in atherosclerotic lesions.

EMBODIMENTS FOR CARRYING OUT THE INVENTION

Figure 1:
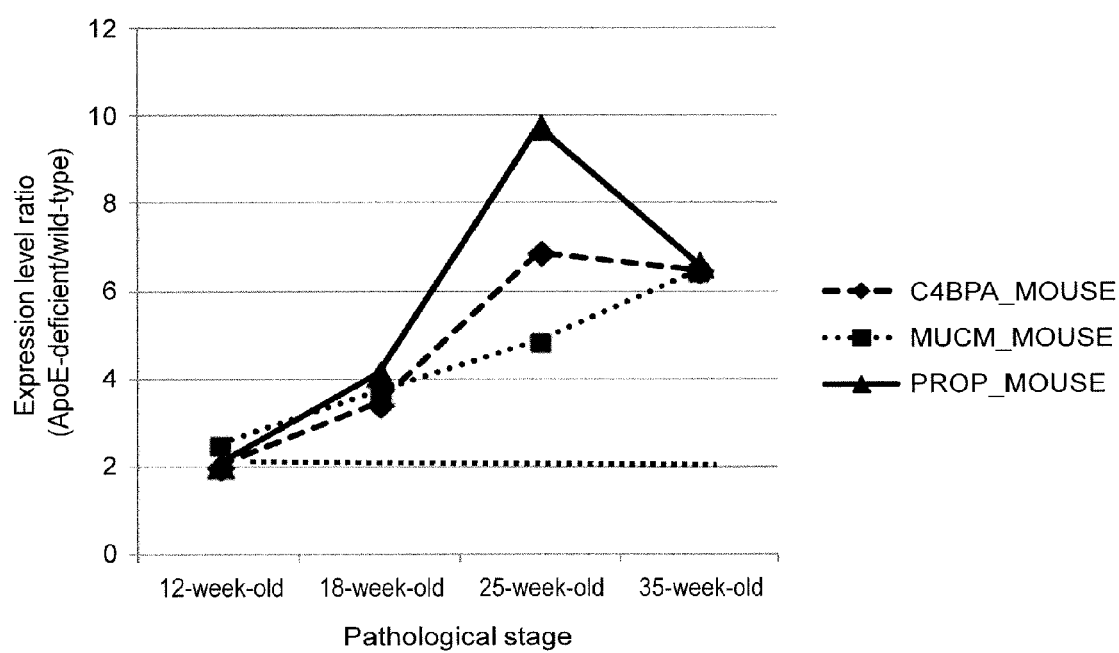
FIG. 1 is a graph showing the ratio of the expression level of a protein group in ApoE-deficient mice divided by that in wild-type mice at each disease stage, by which variation pattern 1 was exhibited.
Figure 2:
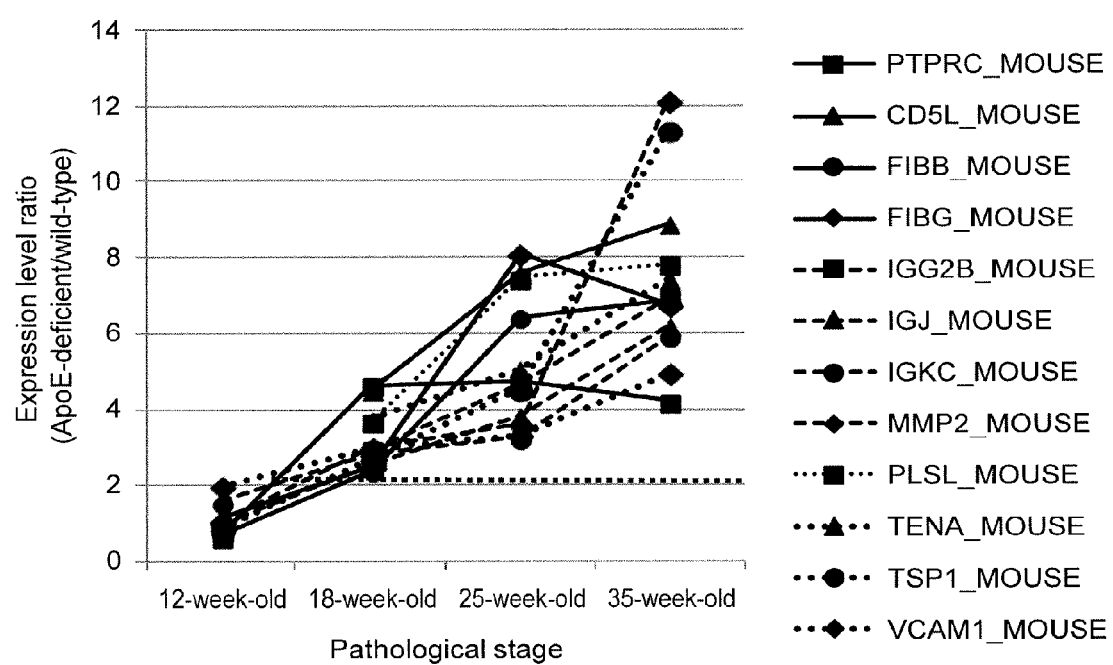
FIG. 2 is a graph showing the ratio of the expression level of a protein group in ApoE-deficient mice divided by that in wild-type mice at each disease stage, by which variation pattern 2 was exhibited.
Figure 3:
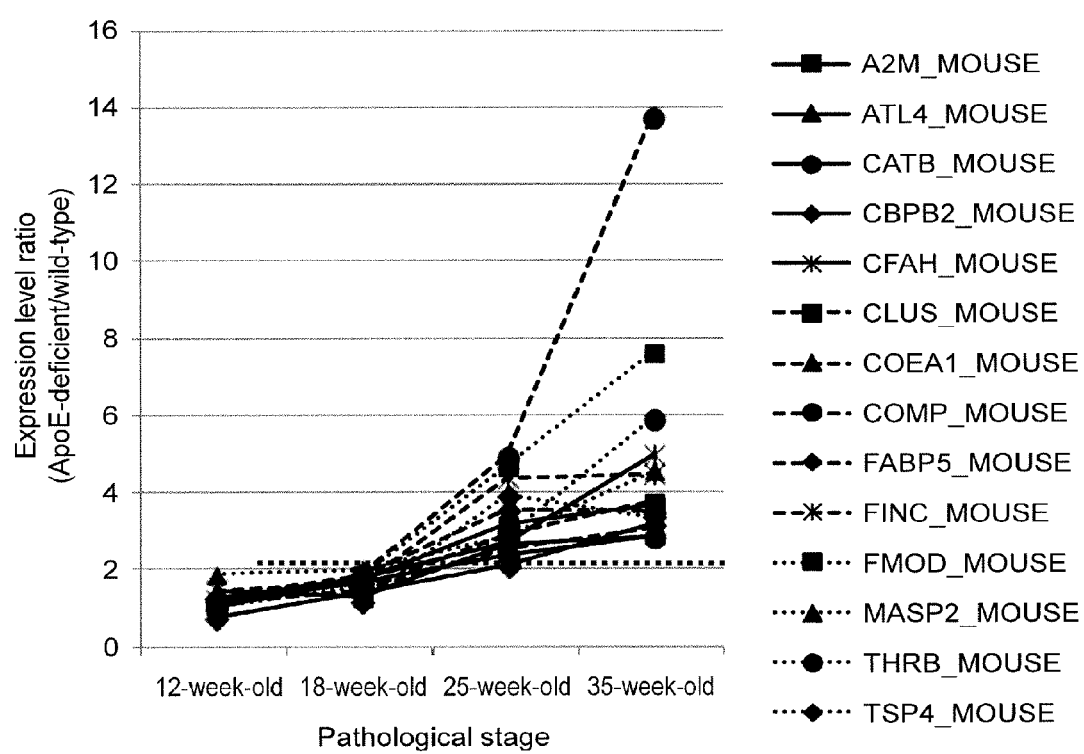
FIG. 3 is a graph showing the ratio of the expression level of a protein group in ApoE-deficient mice divided by that in wild-type mice at each disease stage, by which variation pattern 3 was exhibited.
Figure 4:
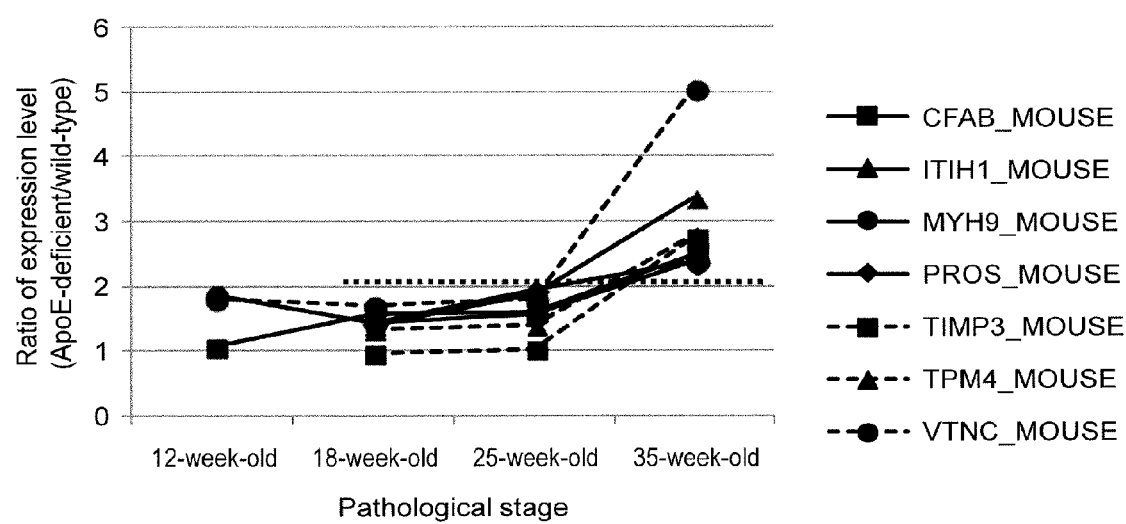
FIG. 4 is a graph showing the ratio of the expression level of a protein group in ApoE-deficient mice divided by that in wild-type mice at each disease stage, by which variation pattern 4 was exhibited.

The present invention is explained in detail below. This application claims a priority of Japanese patent application No. 2010-257065 filed on Nov. 17, 2010 and the content described in the description and/or drawings of this patent application is incorporated herein by reference.

The present invention provides novel markers and marker groups for evaluation and visualization of atherosclerotic lesions. The markers and marker groups provided by the present invention are proteins, the expression levels of which characteristically vary with the progression of atherosclerotic lesions. They are useful for prediction of the onset of diseases associated with arteriosclerosis such as stable angina pectoris and acute myocardial infarction, determination of the stages of atherosclerotic lesions, prediction of prognosis of atherosclerotic lesions, visualization of atherosclerotic lesions, and evaluation of the effectiveness of therapeutic agents or therapeutic methods for diseases associated with arteriosclerosis, for example. Therefore, the method for evaluating atherosclerotic lesions according to the present invention comprises the steps of: detecting a marker protein exhibiting the expression pattern (variation in expression) characteristic to a specific disease stage of an atherosclerotic lesion in a subject; and evaluating the atherosclerotic lesion in the subject based on the detection result.

Subjects to be evaluated according to the present invention are humans and non-human mammals, such as primates (e.g., monkeys and chimpanzees), livestock animals (cattle, horses, pigs, and sheep), pet animals (e.g., dogs and cats), and experimental animals (e.g., mice, rats, and rabbits). Such subjects may also be reptiles and birds.

In addition, the term "marker" as used herein refers to a protein to be detected for evaluation of arteriosclerosis according to the present invention. Also, the term "marker group" refers to a combination comprising two or more markers.

Markers to be used in the present invention are as summarized in the following Table 1 to Table 4. In Table 1 to Table 4, the "Entry name" column and the "Accession No." column are located under the "Mouse" column and the "Human" column, and they show the names and the accession numbers, respectively, of marker proteins of the "Mouse" and the "Human," as in UniProtKB/Swiss-Prot (http://www.uniprot.org/). Table 1 to Table 4 also show the ratios of the expression levels of marker proteins at different disease stages as detected in examples.

TABLE 1

| | Mouse | | Human | | Expression level ratio (ApoE-deficient/wild-type) | | | |
| | | | | | 12-week-old | 18-week-old | 25-week-old | 35-week-old |
| Protein name | Entry name | Accession No. | Entry name | Accession No. | Initial stage | Early intermediate stage | Intermediate stage | Late stage |
|---|---|---|---|---|---|---|---|---|
| Cartilage oligomeric matrix protein | COMP_MOUSE | Q9R0G6 | COMP_HUMAN | P49747 | ND | 0.855 | 4.918 | 13.744 |
| Fibromodulin | FMOD_MOUSE | P50608 | FMOD_HUMAN | Q06828 | ND | 1.838 | 4.668 | 7.632 |
| Fibronectin | FINC_MOUSE | P11276 | FINC_HUMAN | P02751 | 1.474 | 1.634 | 4.358 | 4.468 |
| Thrombospondin-4 | TSP4_MOUSE | Q9Z1T2 | TSP4_HUMAN | P35443 | ND | 1.174 | 3.911 | 3.353 |

TABLE 2

| | Mouse | | Human | | Expression level ratio (ApoE-deficient/wild-type) | | | |
| | | | | | 12-week-old | 18-week-old | 25-week-old | 35-week-old |
| Protein name | Entry name | Accession No. | Entry name | Accession No. | Initial stage | Early intermediate stage | Intermediate stage | Late stage |
|---|---|---|---|---|---|---|---|---|
| Plastin-2 | PLSL_MOUSE | Q61233 | PLSL_HUMAN | P13796 | ND | 3.675 | 7.454 | 7.828 |
| Tenascin | TENA_MOUSE | Q80YX1 | TENA_HUMAN | P24821 | ND | 3.754 | 5.065 | 7.436 |
| CD5 antigen-like protein | CD5L_MOUSE | Q9QWK4 | CD5L_HUMAN | O43866 | ND | 4.512 | 7.573 | 8.895 |
| Properdin | PROP_MOUSE | P11680 | PROP_HUMAN | P27918 | 2.060 | 4.118 | 9.759 | 6.621 |
| C4b-binding protein | C4BPA_MOUSE | P08607 | C4BPA_HUMAN | P04003 | 2.025 | 3.430 | 6.884 | 6.482 |
| Fibrinogen beta chain | FIBB_MOUSE | Q8K0E8 | FIBB_HUMAN | P02675 | 0.678 | 2.383 | 6.418 | 6.834 |

TABLE 2-continued

| | Mouse | | Human | | Expression level ratio (ApoE-deficient/wild-type) | | | |
| --- | --- | --- | --- | --- | --- | --- | --- | --- |
| | | | | | 12-week-old | 18-week-old | 25-week-old | 35-week-old |
| Protein name | Entry name | Accession No. | Entry name | Accession No. | Initial stage | Early intermediate stage | Intermediate stage | Late stage |
| Fibrinogen gamma chain | FIBG_MOUSE | Q8VCM7 | FIBG_HUMAN | P02679 | 1.116 | 2.496 | 8.092 | 6.745 |

TABLE 3

| | Mouse | | Human | | Expression level ratio (ApoE-deficient/wild-type) | | | |
| --- | --- | --- | --- | --- | --- | --- | --- | --- |
| | | | | | 12-week-old | 18-week-old | 25-week-old | 35-week-old |
| Protein name | Entry name | Accession No. | Entry name | Accession No. | Initial stage | Early intermediate stage | Intermediate stage | Late stage |
| Vitronectin | VTNC_MOUSE | P29788 | VTNC_HUMAN | P04004 | 1.785 | 1.699 | 1.789 | 5.031 |
| Matrix metalloproteinase-2 | MMP2_MOUSE | P33434 | MMP2_HUMAN | P08253 | 1.028 | 2.979 | 3.633 | 12.156 |
| Thrombospondin-1 | TSP1_MOUSE | P35441 | TSP1_MOUSE | P35441 | 0.853 | 2.684 | 4.527 | 11.370 |

TABLE 4

| | Mouse | | Human | |
| --- | --- | --- | --- | --- |
| Protein name | Entry name | Accession No. | Entry name | Accession No. |
| membrane-bound form Ig mu chain C region | MUCM_MOUSE | P01873 | IGHM_HUMAN | P01871 |
| Receptor-type tyrosine-protein phosphatase C | PTPRC_MOUSE | P06800 | PTPRC_HUMAN | P08575 |
| Ig gamma-2B chain C region | IGG2B_MOUSE | P01867 | | |
| Immunoglobulin J chain | IGJ_MOUSE | P01592 | IGJ_HUMAN | P01591 |
| Ig kappa chain C region | IGKC_MOUSE | P01837 | IGKC_HUMAN | P01834 |
| Vascular cell adhesion protein 1 | VCAM1_MOUSE | P29533 | VCAM1_HUMAN | P19320 |
| Alpha-2-macroglobulin | A2M_MOUSE | Q61838 | A2MG_HUMAN | P01023 |
| ADAMTS-like protein 4 | ATL4_MOUSE | Q80T21 | ATL4_HUMAN | Q6UY14 |
| Cathepsin B | CATB_MOUSE | P10605 | CATB_HUMAN | P07858 |
| Carboxypeptidase B2 | CBPB2_MOUSE | Q9JHH6 | CBPB2_HUMAN | Q96IY4 |
| Complement factor H | CFAH_MOUSE | P06909 | CFAH_HUMAN | P08603 |
| Clusterin | CLUS_MOUSE | Q06890 | CLUS_HUMAN | P10909 |
| Collagen alpha-1(XIV) chain | COEA1_MOUSE | Q80X19 | COEA1_HUMAN | Q05707 |
| Epidermal fatty acid-binding protein | FABP5_MOUSE | Q05816 | FABP5_HUMAN | Q01469 |
| Mannan-binding lectin associated serine protease 2 | MASP2_MOUSE | Q91WP0 | MASP2_HUMAN | O00187 |
| Prothrombin | THRB_MOUSE | P19221 | THRB_HUMAN | P00734 |
| Complement factor B | CFAB_MOUSE | P04186 | CFAB_HUMAN | P00751 |
| Inter-alpha-trypsin inhibitor heavy chain H1 | ITIH1_MOUSE | Q61702 | ITIH1_HUMAN | P19827 |
| Myosin-9 | MYH9_MOUSE | Q8VDD5 | MYH9_HUMAN | P35579 |
| Vitamin K-dependent protein S | PROS_MOUSE | Q08761 | PROS_HUMAN | P07225 |
| Metalloproteinase inhibitor 3 | TIMP3_MOUSE | P39876 | TIMP3_HUMAN | P35625 |
| Tropomyosin alpha-4 | TPM4_MOUSE | Q6IRU2 | TPM4_HUMAN | P67936 |

| | Ratio of expression level (ApoE-deficient/wild-type) | | | |
| --- | --- | --- | --- | --- |
| Protein name | 12-week-old Initial stage | 18-week-old Early intermediate stage | 25-week-old Intermediate stage | 35-week-old Late stage |
| membrane-bound form Ig mu chain C region | 2.505 | 3.721 | 4.857 | 6.460 |
| Receptor-type tyrosine-protein phosphatase C | 0.676 | 4.633 | 4.738 | 4.202 |
| Ig gamma-2B chain C region | ND | 2.945 | 4.673 | 6.901 |
| Immunoglobulin J chain | ND | 2.519 | 3.860 | 6.182 |
| Ig kappa chain C region | 1.570 | 2.803 | 3.247 | 5.915 |
| Vascular cell adhesion protein 1 | 1.980 | 2.968 | 3.327 | 4.947 |
| Alpha-2-macroglobulin | 1.031 | 1.704 | 3.150 | 3.632 |
| ADAMTS-like protein 4 | 1.430 | 1.275 | 2.633 | 2.853 |
| Cathepsin B | 1.134 | 1.680 | 2.365 | 2.847 |
| Carboxypeptidase B2 | 0.755 | 1.405 | 2.097 | 3.163 |
| Complement factor H | 1.228 | 1.800 | 2.709 | 4.957 |
| Clusterin | ND | 1.497 | 2.883 | 3.743 |

TABLE 4-continued

| | | | | |
|---|---|---|---|---|
| Collagen alpha-1(XIV) chain | 1.110 | 1.470 | 2.504 | 3.057 |
| Epidermal fatty acid-binding protein | 1.282 | 1.837 | 3.547 | 3.471 |
| Mannan-binding lectin associated serine protease 2 | 0.861 | 1.998 | 2.846 | 4.525 |
| Prothrombin | 1.018 | 1.572 | 2.852 | 5.903 |
| Complement factor B | 1.057 | 1.570 | 1.611 | 2.479 |
| Inter-alpha-trypsin inhibitor heavy chain H1 | ND | 1.409 | 1.864 | 3.347 |
| Myosin-9 | 0.876 | 1.438 | 1.569 | 2.374 |
| Vitamin K-dependent protein S | ND | 1.415 | 1.940 | 2.376 |
| Metalloproteinase inhibitor 3 | ND | 0.941 | 1.034 | 2.745 |
| Tropomyosin alpha-4 | ND | 1.329 | 1.408 | 2.785 |

In addition, "12-week-old," "18-week-old," "25-week-old," or "35-week-old" (ApoE-deficient mouse) used in tables and the Description refer to a specific disease stage corresponding to the relevant age in weeks. An association between the age in weeks of an ApoE-deficient mouse and a disease stage has been reported in Nakashima, Y. et al., Arterioscler Thromb. 14:133-140, 1994; Zhao, Y. et al., J. Nucl. Med. 49:1707-1714, 2008, and the like. Specifically, at the age of 12 weeks, thickening of the intima of arteries and lipid accumulation are observed (stage 1). At the age of 18 weeks, foam cells are formed because of lipid accumulation (stage 2). At the age of 25 weeks, many unstable atheromatous plaques are observed extensively in the arteries (stage 3), corresponding to the most dangerous stage in atherosclerotic arteriosclerosis. At the age of 35 weeks, many stable lesions with advanced fibrillization and/or calcification are observed (stage 4). Therefore, in the Description, "12-week-old" (ApoE-deficient mouse) corresponds to the initial stage (lesion) of arteriosclerosis, "18-week-old" corresponds to the early intermediate stage (lesion) of arteriosclerosis, "25-week-old" corresponds to the intermediate stage (lesion) of arteriosclerosis, and "35-week-old" corresponds to the late stage (lesion) of arteriosclerosis.

Proteins shown in Table 1 showed no significant difference in amounts until the mice reached the age of 18 weeks, but were characterized in that (i) the ratio of the amounts thereof in ApoE-deficient mice divided by the amounts thereof in wild-type mice (hereinafter, referred to as "the expression level ratio") at the age of 25 weeks is at least 3, and (ii) the expression level ratio thereof at the age of 25 weeks is at least twice as large as the expression level ratio thereof at the age of 18 weeks. These proteins are also markers showing the risk of plaque rupture at the intermediate stage. With the use of at least one type of these proteins as a marker, whether or not lesions at the age of 18 weeks (early intermediate stage) or later are present, and particularly whether or not there is a risk of plaque rupture can be evaluated based on the expression level of the marker.

Proteins shown in Table 2 are characterized in that: (i) the ratio of the amounts thereof in ApoE-deficient mice divided by the amounts thereof in wild-type mice at the age of 18 weeks is at least 2; (ii) the expression level ratio thereof at the age of 18 weeks is at least 1.3 times as large as the expression level ratio thereof at the age of 12 weeks; (iii) the expression level ratio at the age of 25 weeks is at least 4; and (iv) the expression level ratio at the age of 25 weeks is at least 1.3 times as large as the expression level ratio at the age of 18 weeks. These proteins are marker proteins showing the progression of plaques from the initial stage to the intermediate stage. With the use of at least one type thereof as a marker, whether or not a lesion at the age of 12 weeks (the initial stage) or a lesion at the age of 18 weeks (the early intermediate stage) or later is present can be evaluated based on the expression level of the marker.

Proteins shown in Table 3, and particularly: proteins, for which no significant difference was observed in amount (expression level) until the mice reached the age of 12 weeks, but the amounts thereof in ApoE-deficient mice increase to twofold or more than the amounts thereof in wild-type mice at the age of 18 weeks and older; and proteins, for which no significant difference is observed in amount (expression level) until the mice reached the age of 25 weeks, but the amounts thereof in ApoE-deficient mice increase to two fold or more than the amounts thereof in wild-type mice at the age of 35 weeks is at least, are characterized in that: (i) the expression level ratio at the age of 35 weeks is at least 4; and (ii) the expression level ratio at the age of 35 weeks is at least twice as large as the expression level ratio at the age of 25 weeks. These proteins were marker proteins indicating the stabilization of plaques at the late stage. With the use of at least one type of these proteins as a marker protein, the presence or the absence of a lesion at the age of 35 weeks (the late stage) or later can be evaluated based on the expression level of the marker.

Proteins shown in Table 4 are marker proteins, the expression levels of which in ApoE-deficient mice are varied depending on ages in weeks compared with those in wild-type mice. Of these proteins, at least one type thereof can be used as a marker, or this can be used in combination with markers shown in Table 1 to Table 3. Thus, the presence or the absence of a lesion at each age in week (at the initial stage, the early intermediate stage, the intermediate stage, or the late stage) can be evaluated based on the expression level(s) of the marker(s).

In the present invention, atherosclerotic lesions can be evaluated by detecting at least one type of markers shown in at least Table 1. Specifically, the presence or the absence of an atherosclerotic lesion with a risk of plaque rupture can be evaluated using each marker in Table 1. Furthermore, according to the present invention, at least two markers are used in combination, making it possible to more precise and highly accurate evaluation of atherosclerotic lesions. For example, at least one type of protein shown in Table 1 (cartilage oligomeric matrix protein, fibromodulin, fibronectin, or thrombospondin-4) and, among each group shown in Table 2 to Table 4, at least two types of protein selected from at least one, at least two, or at least three groups are combined.

For example, marker(s) shown in Table 1 and marker(s) shown in Table 2 are used in combination. Thus, differentiation becomes possible, such as whether the lesion is at the initial stage (12-week-old), the early intermediate stage (18-week-old), the intermediate stage (25-week-old), or later, based on the expression level(s) of the marker(s). Furthermore, a marker(s) shown in Table 1 and a marker(s) shown in Table 3 are used in combination. Thus, differentiation becomes possible such that if the lesion is at the intermediate stage (25-week-old), the late stage or later (35-week-old), based on the expression levels of these markers. Furthermore, a marker(s) shown in Table 1 and a marker(s) shown in Table 4 are used in combination. Thus, differentiation becomes possible such that if the lesion is at the initial stage (12-week-old), the early intermediate stage (18-week-old), the intermediate stage (25-week-old) or the late stage (35-week-old), based on the expression levels of these markers.

Alternatively, three or more markers shown in Table 1 to Table 4 can be used in combination. For example, at least one marker each was selected from each one of Table 1 to Table 4 and then the markers are used in combination. Thus, detailed and precise differentiation becomes possible, such that if a lesion is at the initial stage (12-week-old), the early intermediate stage (18-week-old), the intermediate stage (25-week-old), or the late stage (35-week-old) based on the expression levels of these markers. Preferably, three or more markers, and more preferably, three to seven markers are combined. Such a combination can be adequately selected in accordance with subject type, sex, age, purpose of evaluation of arteriosclerosis, disease stage to be subjected to evaluation, and the like.

As described above, the above markers or marker groups are expressed in patterns characteristic to specific disease stages of atherosclerotic lesions. Therefore, in the method for evaluating an atherosclerotic lesion according to the present invention, the above markers or marker groups in a subject are detected. When two or more markers are detected, the steps of detecting each marker can be performed simultaneously or at different times. Also, in the present invention, the term "detection of marker (group)" may refer to the detection of a marker protein, a substance derived therefrom, or a derivative thereof, or a gene (mRNA) encoding the protein. The term "substance derived therefrom" and "a derivative thereof" refer to a substance derived or originated from a marker protein. Examples thereof include, but are not limited to, a protein containing a signal peptide, a specific subunit molecule of a protein, a modified protein, and a protein fragment. For example, fibrinogen shown in Table 2 contains β chain and γ chain, and an intact molecule of fibrinogen may be detected, or any one of β chain or γ chain that is a substance derived therefrom may be detected in the present invention.

Detection of a marker protein preferably relates to semi-quantitative or quantitative measurement of the amount or the concentration of the marker protein in a subject. The amount may be the absolute quantity or the relative quantity. Detection can be performed directly or indirectly. Direct detection relates to measurement of the amount or the concentration of a marker protein or mRNA existing in a subject based on a signal directly correlating with the number of molecules of the marker protein or mRNA. Such a signal is based on specific physical or chemical properties of a protein or mRNA, for example. Indirect measurement is measurement of signals obtained from secondary components (that is, components other than marker proteins or mRNA) such as ligands (e.g., antibodies), labels, or enzymatic reaction products.

The step of detecting a marker protein can be performed by administering to a subject a substance specifically binding to a marker protein, and then detecting the substance bound to the marker protein existing in the subject, for example. Alternatively, the step of detecting a marker protein can be performed by preparing a subject-derived sample, bringing the sample into contact with a substance specifically binding to a marker protein, and then detecting the binding of the marker protein with the substance.

The term "substance specifically binding to a marker protein" refers to a substance that binds to a marker protein, a substance derived therefrom, or a derivative thereof with high affinity, but binds (with only low affinity) or never bind to molecules unrelated to a marker protein, a substance derived therefrom, or a derivative thereof. Examples of such a substance include antibodies, antibody-like molecules, nucleic acid aptamers, substrates and other ligands. Preferably, a substance specifically binding to a marker protein is an antibody or an antibody fragment. For example, an antibody against each marker protein may be either a monoclonal antibody or a polyclonal antibody, or may be particularly Fab, Fab', F(ab')$_2$, scFv, Fv fragment, or the like that can bind to an epitope of each marker protein. An antibody and an antibody-like molecule can be prepared by methods known in the art or can be obtained as a commercially available product. An antibody-like molecule is a protein fragment containing a peptide equivalent to an antibody variable region capable of binding to a marker protein, which is prepared by a non-immunological technique such as a phage display method or a combinatorial chemistry method. An example thereof is an affibody. An antibody-like molecule is effective in a case where preparation of an antibody with a general immunization method is difficult because of high toxicity. A nucleic acid aptamer is known in the art and is a nucleic acid molecule capable of specifically binding to a specific protein (specifically, a marker protein). Such a nucleic acid aptamer can be chemically synthesized in vitro and is advantageous in that it has low immunogenicity. A nucleic acid aptamer can be designed by a SELEX method or the like. Persons skilled in the art can design and synthesize an appropriate nucleic acid aptamer. When a marker protein has enzyme activity, the substrate or the substrate derivative thereof can be used as a substance capable of specifically binding to the enzyme. For example, when a marker protein is protease, a protease inhibitor (may be the one derived from nature or a synthetic molecule) can be used. When a marker protein is a receptor, a ligand thereof (an agonist, an antagonist, and a derivative thereof) can be used as a substance specifically binding to the receptor. In particular, in the case of a receptor localized in cell membrane, a ligand-binding site is located extracellularly, and thus the receptor is advantageous in that a ligand to be administered to a subject can easily bind from outside the cell to the receptor.

When a marker protein is detected by administration of a substance specifically binding to the marker protein to a subject, the substance specifically binding to the marker protein binds to the marker protein in vivo in the subject when administered to the subject. Therefore, with the use of such a substance, localization of a marker protein in a subject can be examined and the location and disease stage of an atherosclerotic lesion(s) can be evaluated, for example. Moreover, such a substance is bound to a contrast medium in advance, making it possible to visualize the atherosclerotic lesions in the subject.

A marker protein can be conveniently and noninvasively detected using such an agent for visualization. Therefore, the present invention also provides an agent for visualizing an atherosclerotic lesion. The agent for visualization contains a substance specifically binding to at least one type of marker protein and a contrast medium. As a contrast medium, an arbitrary contrast medium known in the in vivo imaging field can be used. Examples of such a contrast medium include: fluorescent substances such as fluorescein, FITC, and fluorescence emitting metals (e.g., $^{152}$Eu, and lanthanum series); chemical or biological luminescent substances such as luminol, imidazole, luciferin, luciferase, and green fluorescent protein (GFP); radioactive substances such as $^{99m}$Tc, $^{123}$I, $^{131}$I, $^{97}$Ru, $^{67}$Cu, $^{11}$C, and $^{13}$N; paramagnetic isotopes such as $^{153}$Gd, $^{157}$Gd, $^{55}$Mn, $^{162}$Dy, $^{52}$Cr, $^{56}$Fe, and superparamagnetic iron oxide particles; and other contrast media such as gadolinium, gadolinium complexes, iodo contrast media, liposomes, micelles, cells, virus particles, viruses, microparticles, nanoparticles, microdevices with spaces, emulsions, lipid discs, polymers, perfluorocarbon nanoparticles, and ultrafine bubbles. A substance specifically binding to a marker protein can be bound to a contrast medium by a method known in the art. For example, such a substance and a medium can be directly chemically bound or indirectly bound via an appropriate linker.

A medicine to be used in the present invention containing the above agent for visualizing an atherosclerotic lesion may contain, in addition to a substance specifically binding to a marker protein, a pharmaceutically acceptable carrier or additive. Examples of such a carrier or an additive include water, a pharmaceutically acceptable organic solvent, collagen, polyvinyl alcohol, polyvinylpyrrolidone, carboxyvinyl polymer, sodium alginate, water-soluble dextran, sodium carboxymethyl starch, pectin, xanthan gum, gum Arabic, casein, gelatin, agar, glycerin, propylene glycol, polyethylene glycol, Vaseline (petroleum jelly), paraffin, stearyl alcohol, stearic acid, mannitol, sorbitol, and lactose. An additive to be used herein can be adequately selected or selected in combination depending on dosage forms.

The method for administration of the medicine of the present invention is not particularly limited. The medicine can be administered via peroral administration or parenteral administration such as subcutaneous administration, intradermal administration, intramuscular administration, intravenous administration, transdermal administration, rectal administration, and intranasal administration.

When the medicine of the present invention is administered via peroral administration, it may be in the form of tablets, capsules (e.g., hard capsules, soft capsules, and microcapsules), granules, powders, pills, troches, pharmaceutical solution as internal medicine, liquid agents, suspensions, emulsions, syrups, or the like. The medicine may also be a dry product that is dissolved again when it is used. Also, when the medicine of the present invention is administered via parenteral administration, examples of dosage forms that can be selected herein include injection preparations (e.g., solutions, emulsions, and suspensions) for intravenous injection (including drip infusion), intramuscular injection, intraperitoneal injection, and subcutaneous injection, and external preparations such as ointments (particularly, an ointment for eyes), cream pharmaceuticals, suppositories, adhesive skin patches, eye drops, nasal drops, inhalers, liniments, and aerosol. In the case of injection preparations, they are provided in unit dosage ampules or vessels for high dose administration.

These various preparations can be produced by conventional methods by appropriately selecting an excipient, an extending agent, a binder, a wetting agent, a disintegrator, a lubricant, a surfactant, a dispersing agent, a buffering agent, a pH adjuster, a preservative, a solubilizing agent, an antiseptic, a taste and flavor corrigent, an absorption accelerator, a soothing agent, a stabilizer, a tonicity agent, and the like that are generally used in medicaments.

The amount of a substance specifically binding to a marker protein that is to be incorporated into the medicine of the present invention, differs depending on the type of substance, the type of contrast medium to be bound with the substance, the purpose of use thereof, dosage form, the route of administration, and the like. For example, the amount ranges from 1% to 99% of the total weight, and preferably ranges from 5% to 90% of the total weight.

Also, the dose and the dosing interval of the medicine of the present invention differ depending on the type of a substance specifically binding to a marker protein, the type of a contrast medium to be bound with the substance, a subject of administration, the age and the body weight of a subject, the route of administration, and the frequency of administration. The dose and the dosing interval thereof can be varied widely.

In the case of an agent for visualizing an atherosclerotic lesion, after administration of the medicine, the presence or the location of a substance specifically binding to a marker protein in a subject is visualized using a contrast medium as an indicator. Preferably, the presence or the location of a substance specifically binding to a marker protein is visualized by a known imaging technique. Such an imaging technique differs depending on a label to be used herein, the type of a subject, a site for imaging, and the like. Positron emission tomography (PET), single photon emission computed tomography (SPECT), γ scintigraphy, autoradiography, fluorescent imaging, magnetic resonance imaging (MRI), ultrasonication, computed tomography (CT), and other in vivo imaging systems can be used. Thus, based on such a contrast medium to which a substance specifically binding to a marker protein has been bound, the presence or the location of an atherosclerotic lesion in the subject can be visualized and determined.

In addition to the above-visualized presence or the location of a marker protein, determination of the disease stage of an atherosclerotic lesion, prediction of the prognosis of an atherosclerotic lesion, and evaluation of the therapeutic effect against arteriosclerosis in a subject, and the like can also be evaluated based on the type and the amount of the marker protein.

Moreover, visualization of an atherosclerotic lesion as described above makes it possible to conveniently and precisely specify a lesion site upon surgery.

Another embodiment that involves preparing a subject-derived sample and detecting a marker protein is explained as follows. Samples to be used herein are not particularly limited, as long as they are samples derived from subjects to be evaluated for atherosclerotic lesions. Samples are adequately selected in accordance with methods or types of means of detecting markers. Examples thereof include tissue or cell samples (e.g., arterial tissues and cells). Also, a tissue or cell sample is preferably frozen and cryopreserved immediately after collection by a method known or generally used in the art using liquid nitrogen, dry ice, or the like.

In an embodiment of the present invention, a marker protein can be detected by a means of measuring the amount of a protein in a sample. Such means are known in the art, such as immunoassay methods and reagents. Also, a marker protein can be detected by a means of measuring physical or chemical properties peculiar to the marker protein, such as a means of measuring accurate molecular weights, rNMR spectra, or the like. Examples of a means of detecting a marker protein include analyzers such as a biosensor, a protein chip, an optical unit combined with immunoassay, a mass spectrometer, an NMR analyzer, a 2D electrophoresis apparatus, and a chromatography apparatus.

In a preferred embodiment, a marker protein can be detected using mass spectrometry (MS). In particular, analysis made by a mass spectrometer combined with liquid chromatography (LC/MS) is sensitive and thus is advantageous. As labels, isotope labeling reagents known in the art can be used. Appropriate labeling reagents can be commercially obtained. Also, fractionation can be performed by a method known in the art. For example, fractionation can be performed using a commercially available strong cationic column or the like.

In another embodiment, a marker protein in a sample can be detected by immunoassay (immunological assay). Specifically, the protein in a sample is detected based on a reaction between the marker protein in the sample and an antibody specifically binding to the protein. Immunoassay may be performed with either a liquid phase system or a solid phase system, as long as the method is generally employed in the art. In view of ease of detection, a solid phase system is preferably used. The forms of immunoassay are not limited and may be, in addition to a direct solid phase method, a sandwich method, a competition assay, a Western blotting method, an ELISA (enzyme linked immunosorbent assay) method, or the like.

An antibody (to be used in the method of the present invention) against each marker protein may be either a monoclonal antibody or a polyclonal antibody, or may be Fab, Fab', F(ab')$_2$, scFv, Fv fragment, or the like capable of binding to the epitope of each marker protein. When a primary antibody and a secondary antibody are used, both antibodies may be monoclonal antibodies. Alternatively, either a primary antibody or a secondary antibody may be a polyclonal antibody. Such an antibody can be prepared by a method known in the art or can be commercially obtained.

Binding of a marker protein with an antibody can be measured according to a known method. Persons skilled in the art can determine an effective and optimum measurement method for each assay according to the type and form of immunoassay to be employed, or the type of a label to be used herein, for example. For example, for easy detection of the binding of a marker protein in a sample with an antibody, the binding is directly detected by labeling the antibody, or the binding is indirectly detected using a labeled secondary antibody, a biotin-avidin conjugate, or the like.

With a solid phase system, an antibody or a protein component in a sample is immobilized onto a solid phase (e.g., a plate, a membrane, or beads), and then immunological binding of a marker protein with a solid is tested on the solid phase. Such a solid phase is not particularly limited, as long as it is conventionally used in the art. For example, a commercially available nitrocellulose membrane or PVDF membrane can be used. An antibody or a protein component in a sample is immobilized on a solid phase, so that unbound components in the sample or a reagent can be easily removed. Also, in particular, in the case of a protein array method using a membrane with dozens of types of antibody immobilized thereto, the presence of many types of marker protein can be analyzed within a short time using a small amount of a subject-derived sample (e.g., plasma). Such immunoassay can also be performed with test strips, the operation with which can be conveniently performed.

When liquid-phase immunoassay is selected, for example, a labeled antibody is brought into contact with a sample so as to bind the labeled antibody to a marker protein, the conjugate is separated, and thus the signal of the label is detected. Alternatively, an antibody (primary antibody) against a marker protein is brought into contact with a sample so as to bind the primary antibody to the marker protein, a labeled antibody (secondary antibody) is bound to the conjugate, and thus the signal of the label is detected from the conjugate of these three substances. Alternatively, for further enhancement of signals, an unlabeled secondary antibody is first bound to an antibody+marker protein conjugate, so as to bind a labeling substance to the secondary antibody. Such binding of a labeling substance to a secondary antibody can be performed by biotinylating the secondary antibody and avidinylating the labeling substance in advance, for example.

A marker protein can also be detected in situ, as in the case of using an immunohistochemical staining method (e.g., an immunostaining method) or immunoelectron microscopy. In situ detection can be performed by excising a histological sample from a subject (e.g., a biopsy sample and a tissue paraffin embedded section), and then bringing a labeled antibody or antibody fragment into contact therewith.

As labels for labeling antibodies to be used in immunoassay, enzymes, radio isotopes, fluorescent dyes, or avidin-biotin systems can be used. As enzymes, enzymes that are used for general enzyme immunoassay (EIA) can be used, such as peroxidase, β-galactosidase, and alkaline phosphatase. Also, an enzyme inhibition substance, a coenzyme, and the like can be used. Binding of these enzymes with antibodies can be performed by known methods using cross-linking agents such as a maleimide compound. As radio isotopes, $^{125}$I, $^3$H, and the like, which are used for general radio immunoassay (RIA), can be used. As fluorescent dyes, fluorescein isothiocyanate (FITC), tetramethylrhodamine isothiocyanate (TRITC), and the like, which are used for general fluorescent antibody techniques, can be used.

The signal of a label can also be detected according to a method known in the art. For example, when an enzyme label is used, a substrate that is degraded by enzymatic action to develop color is added, the amount of the substrate degraded is optically measured to find enzyme activity, the resulting value is converted to the amount of the antibody bound, the result is compared with a standard value, and thus the amount of the antibody is calculated. A substrate differs depending on the type of enzyme to be used herein. For example, when peroxidase is used as an enzyme, 3,3',5,5'-tetramethylbenzidine can be used as a substrate, and when alkaline phosphatase is used as an enzyme, para-nitrophenol or the like can be used as a substrate. When a radioactive label is used, the radiation dose from the radioactive label is measured by a scintillation counter or the like. A fluorescent label can be detected or quantitatively determined using a fluorescent microscope, a plate reader, a fluorescent imaging apparatus, or the like.

As described above, a marker protein in a subject-derived sample is detected, and then arteriosclerotic lesion(s) in the subject can be evaluated based on the results.

The term "evaluation of atherosclerotic lesions" as used herein refers to determination of the presence of atherosclerotic lesions in a subject, determination of the stage of atherosclerotic lesions existing in a subject, determination of the location of atherosclerotic lesions existing in a subject, evaluation of therapeutic effects on arteriosclerosis existing in a subject, and prediction of the prognosis of arteriosclerosis existing in a subject. Also, the term "evaluation" in the present invention is meant to include continuous monitoring of arteriosclerosis that has already been evaluated or diagnosed and confirmation of the past evaluation or diagnosis of arteriosclerosis.

Moreover, through evaluation of atherosclerotic lesions, the risk of developing diseases associated with arteriosclerosis, such as angina pectoris (e.g., stable angina pectoris), acute myocardial infarction, brain infarction, encephalorrhagy, cerebral thrombosis, cerebral embolism, aortic aneurysm, obstructive arteriosclerosis, and acute coronary syndromes can also be evaluated.

Persons skilled in the art understand that accurate results cannot be always obtained for all (that is, 100% of) subjects to be evaluated by the present invention (evaluation is an object of the present invention). In the present invention, the "evaluation" is intended to allow evaluation of subjects accounting for a statistically significant proportion of all subjects. Such a statistically significant proportion can be determined using various known statistical evaluation tools such as determination of a confidence interval, determination of p value, student's t-test, Mann-Whitney test, and the like. A preferable confidence interval is at least 90%. The p value is preferably 0.1, 0.01, 0.005, or 0.0001. More preferably, at least 60%, at least 80%, or at least 90% of subjects can be appropriately evaluated by the present invention.

When evaluation is performed, the detection result of a marker protein in a subject is compared with a standard level. Such a standard level is: the measured level of a marker protein in a healthy-subject-derived sample, the measured level of a marker protein in a sample from a subject diagnosed as having arteriosclerosis at a specific stage, the measured level of a marker protein in a sample from a subject before treatment, or the like. A standard level for an individual subject may be varied depending on various physiological parameters such as subject type, age, and sex.

Preferably, individual subjects with arteriosclerosis are classified according to the degree of the progression of the disease (stage), and the expression levels of marker proteins are obtained from individual subjects belonging to each stage and individual subjects in a normal state. Then, correlations between variations in the expression of a marker protein and progression stages are recorded into an expression profile database. The ratio of the expression level of a marker protein in a subject-derived sample divided by the expression level thereof in a standard sample (prepared in advance) is measured. The expression profile database can be referred for the thus obtained measured value. Such an expression profile database is useful as "standard levels" or "standard range" that can be indicators of the presence or the absence of arteriosclerosis in a subject, the progression stage, and the onset or the degree of progression of arteriosclerosis. Such a standard level may be the only one cutoff value (e.g., average value or median value), or standard levels may be within a specific range (e.g., quartile). When evaluation is performed using a database, for example, the ratio of the expression level R(i) of a protein in a subject-derived sample to the same in a standard sample is measured. One, two, or more marker proteins (i=1–N) thereof are subjected to measurement. Each of these measured values is compared with the value at each progression stage (Rj(i), wherein "j" denotes stage No. ranging from 0-4) and then the results are recorded in the database, so that the progression stage of arteriosclerosis in the subject can be determined. Comparison can be performed by finding stage "j" at which the result of $\Sigma\{R(i)-Rj(i)\}^2 (i=1-N)$ is minimum, for example.

In addition, when evaluation is performed using a human as a subject, a standard level is also preferably the measured expression level of a marker protein in a human. A standard level obtained with the use of experimental animals such as mice can also be extrapolated.

Specific examples of evaluation of arteriosclerosis are as follows. The level of a marker protein shown in Table 1 in a subject, which is higher than a standard level, indicates the presence of atherosclerotic lesions at the intermediate stage or later in the subject. Also, the level of a marker protein shown in Table 2 in a subject, which is higher than a standard level, indicates the presence of atherosclerotic lesions at the initial or early intermediate stage or later in the subject. The level of a marker protein shown in Table 3 in a subject, which is higher than a standard level, indicates the presence of atherosclerotic lesions at the late stage or later in a subject. Marker proteins shown in Table 4 in a subject are combined with other marker proteins, and then variations in the expression levels thereof are examined, indicating the presence of atherosclerotic lesions in the subject.

Furthermore, the method for evaluating atherosclerotic lesions according to the present invention may be performed in combination with other known diagnosis methods for arteriosclerosis. Examples of such known diagnosis methods for arteriosclerosis include measurement of physiological and biochemical markers of arteriosclerosis (e.g., high blood pressure, cholesterol level, and triglyceride level), measurement with electrocardiogram, measurement of arterial pulse wave velocity (PWV), and angiography.

Furthermore, the method for evaluating atherosclerotic lesions of the present invention can also be combined with other arteriosclerosis markers. For example, the present inventors have revealed that: an increase in the expression level of von Willebrand factor and/or a decrease in the expression level of complement factor D in blood plasma can be an indicator for arteriosclerosis at the early intermediate stage; and an increase in the expression level of complement component C8 and/or a an increase in the expression level of vitamin K-dependent protein Z in blood plasma can be an indicator for arteriosclerosis at the intermediate stage (WO 2011/136080). Moreover, as arteriosclerosis markers in blood plasma, a CD5 antigen-like protein and an immunoglobulin mu chain C region exhibited maximum expression levels at the early intermediate stage, and a blood plasma protease C1 inhibitor, thrombospondin-4, fetuin-B, and complement factor H exhibited minimum expression levels at the early intermediate stage or the intermediate stage. Heparin cofactor 2, alpha-2-macroglobulin, complement component C9, vitamin K-dependent protein C, antithrombin-III, EGF-containing fibrin-like extracellular matrix protein 1, inter alpha trypsin inhibitor heavy chain H1, inter alpha trypsin inhibitor heavy chain H2, and properdin exhibited decreased expression levels with the progression of the disease stage. Complement C1q subcomponent subunit B exhibited the expression level that increased with the progression of the disease stage. Therefore, the above blood plasma arteriosclerosis markers are used in combination with the evaluation of atherosclerotic lesions of the present invention, so that evaluation can be performed with higher accuracy.

The presence of atherosclerotic (unstable) lesions can be determined at an early stage by the method for evaluating atherosclerotic lesions according to the present invention. Specifically, the present invention enables determination of the presence or the absence of unstable atherosclerotic lesions, which cannot be recognized by currently available diagnostic techniques or criteria. Also, when atherosclerotic lesions are present, the disease stage and the location of each lesion can be specified in detail. Accordingly, the subject can timely receive treatment (for diseases associated with arteriosclerosis such as angina pectoris, myocardial infarction, and brain infarction) suitable for the disease stage thereof precisely. The method of the present invention is also advantageous in that arteriosclerosis can be reliably and rapidly evaluated by techniques with low invasiveness.

The method for evaluating atherosclerotic lesions according to the present invention can be easily and conveniently performed using a kit and/or an apparatus provided with a means of detecting the above markers.

The kit for evaluating atherosclerotic lesions according to the present invention contains at least one type of substance specifically binding to at least one type of protein selected from at least group (a) from among proteins shown in the following groups (a) to (d):
(a) cartilage oligomeric matrix protein, fibromodulin, fibronectin, and thrombospondin-4;
(b) plastin-2, tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4.

An example of the kit of the present invention is composed of antibodies specifically binding to marker proteins, contrast media or labels, buffers for dilution and washing, and if necessary labeled secondary antibodies, substrate reagents for causing color development, luminescence and fluorescence generation, manuals describing procedures and evaluation methods, and the like. When a marker protein in a subject is detected in vivo, the kit may further contain a means of administration, such as vials, ampules, and syringes. When a marker protein in a subject-derived sample is detected, an antibody immobilized on a solid-phase support (e.g., a membrane or beads) may be used.

The kit of the present invention may contain instructions in which procedures and protocols for implementing the method of the present invention are described and tables showing standard levels or reference ranges to be employed for evaluation of arteriosclerotic lesions, for example.

Components contained in the kit of the present invention may be individually provided or provided within a single container. Preferably, the kit of the present invention contains all the components required for implementation of the method of the present invention, as components with adjusted concentrations, for example, so that they can be used immediately.

The apparatus for evaluating atherosclerotic lesions according to the present invention comprises the following means of:
(i) detecting at least one type of protein selected from at least group (a) from among proteins shown in the above groups (a) to (d), in a subject; and
(ii) evaluating an atherosclerotic lesion in the subject based on the detection result obtained by means (i).

The apparatus of present invention may further comprise the following means of:
(iii) storing the standard levels of the above proteins; and
(iv) comparing the detection results of proteins in a subject with the standard levels.

Figure 5:
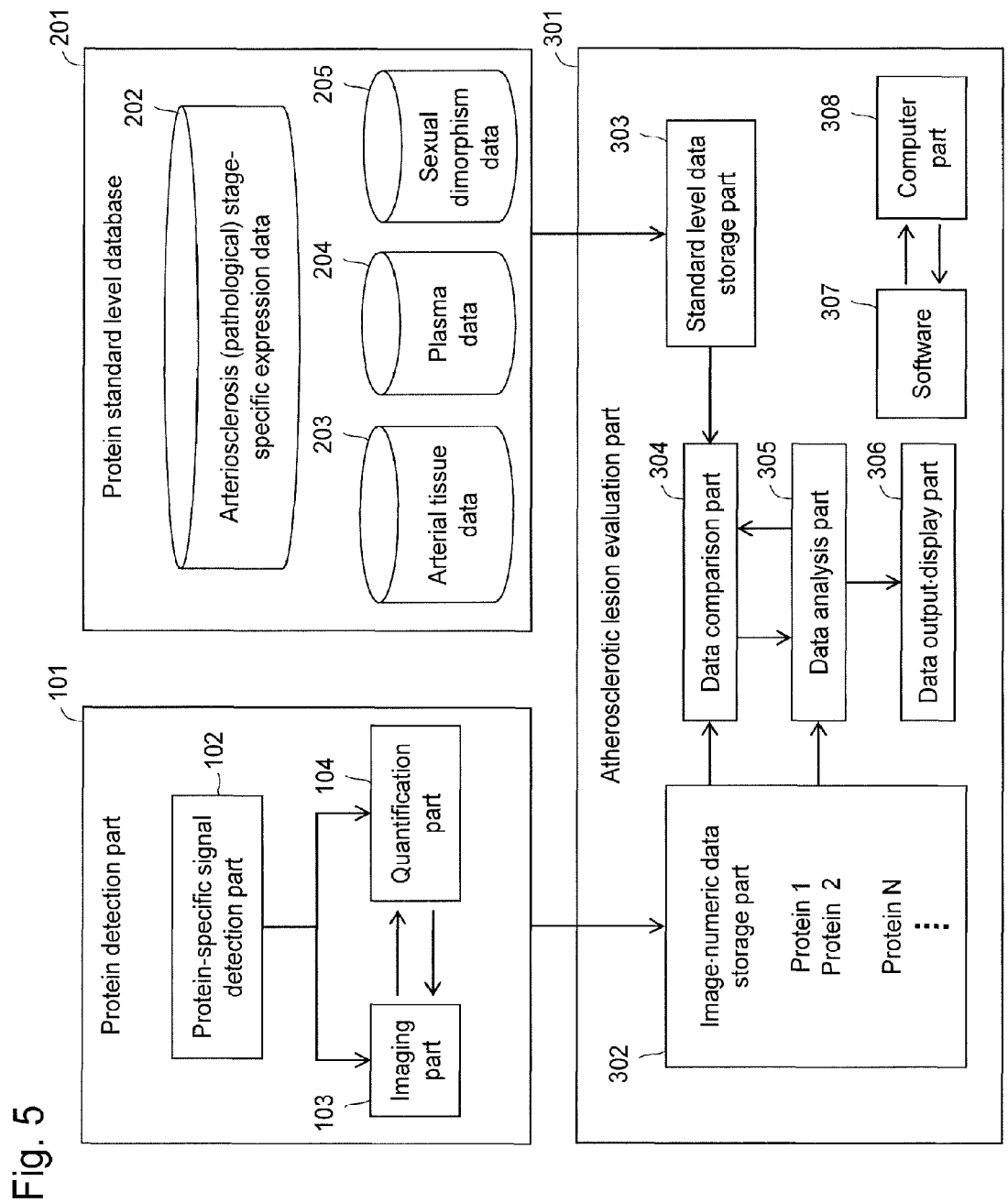
FIG. 5 shows the outline of the apparatus of the present invention for evaluating atherosclerotic lesions.

The apparatus of the present invention is a system, wherein the means (i) and (ii) are combined with further preferably means (iii) and (iv) so that the means can be implemented in a mutual manner, so as to be able to perform the method of the present invention. FIG. 5 shows the outline of the apparatus of the present invention.

The means (i) can be a protein detection part 101 provided with a quantification part 104 for detecting and quantifying signals following the operation of a protein specific signal detection part 102 (e.g., mass spectroscopy part), or a quantification part 104 or a imaging part 103 for detecting, quantifying or imaging signals from radioactivity, color development, luminescence, or fluorescence, for example. Also, the means (ii) can be a part 301 for evaluation of atherosclerotic lesions, which is provided with an image•numeric data storage part 302 for storing the detection results (images•numeric data) obtained from the detection part 101, for example, a software 307 for processing the detection results, and a computer part 308. A preferable apparatus is an apparatus that can be used without the knowledge of an experienced clinician. A specific apparatus comprises the detection part 101 (provided with a protein-specific signal detection part 102 such as PET, SPECT, γ scintigraphy, autoradiography, fluorescent imaging, MRI, ultrasonication, CT, a biosensor, a solid-phase support to which an antibody against a marker has been immobilized, mass spectroscopy, a surface plasmon resonance sensor, and an NMR analyzer), and an evaluation part 301 (e.g., an image•numeric data storage part 302, standard level data storage part 303, a data comparison part 304 and a data analysis part 305 for analysis of data, data output•display part 306, a software 307 and a computer unit for activating a computer part 308).

Furthermore, the means (iii) can be a protein standard level database 201, which is provided with expression data 202 containing pathological (arteriosclerosis) stage-specific expression data and may also be provided as necessary with at least one type of data selected from among arterial tissue data 203, blood plasma data 204, and data of differences in males and females 205. Necessary data are loaded from the standard level database 201 to the standard level data storage part 303 of the means (ii), and then the standard level data and the data of image•numeric data storage part 302 are compared and analyzed.

Further in the present invention, a compound or a molecule such as a drug or a prodrug is bound to a substance specifically binding to a marker protein, instead of a contrast medium, and thus the compound or the molecule can be delivered to a site of a subject where the marker protein is present; that is, an atherosclerotic lesion. Examples of such a drug or prodrug include known thrombolytic agents (e.g., urokinase, streptokinase, and a tissue plasminogen activator). Such a targeting agent for delivery of such a drug or a prodrug to an atherosclerotic lesion is also encompassed within the present invention. Such a targeting agent has the effects of: binding to a marker protein existing in an atherosclerotic lesion so as to be able to deliver a compound or a molecule (e.g., a drug or a prodrug) to an atherosclerotic lesion, remaining for a long time within the atherosclerotic lesion, and thus allowing the drug effects to be continuously exhibited for a long time. Therefore, the targeting agent of the present invention can be used as an agent for prevention or treatment of arteriosclerosis. Specifically, the effective dose of the targeting agent of the present invention is administered to a subject, so that arteriosclerosis in the subject can be prevented or treated.

A subject to which the targeting agent of the present invention is administered is not particularly limited. Examples thereof include mammals such as humans, domestic animals (e.g., cattle and pigs), pet animals (e.g., dogs and cats), and experimental animals (e.g., mice, rats, and monkeys). In particular, the target agent is preferably used for a subject suspected of having arteriosclerosis and a subject having arteriosclerosis.

Examples of arteriosclerosis to be treated or prevented in the present invention include, but are not limited to, arteriosclerosis and diseases associated with arteriosclerosis such as angina pectoris (e.g., stable angina pectoris), acute myocardial infarction, brain infarction, encephalorrhagy, cerebral thrombosis, cerebral embolism, aortic aneurysm, obstructive arteriosclerosis, and acute coronary syndromes.

The targeting agent of the present invention can be prepared and administered in a manner as described above in the case of an agent for visualization. Persons skilled in the art can adequately select methods in view of a compound or a molecule (e.g., a drug or a prodrug) to be contained in the targeting agent.

Furthermore, the effectiveness of therapeutic agents or therapeutic methods for arteriosclerosis can be evaluated and test therapeutic agents for arteriosclerosis can be screened for using the above markers or marker groups. Specifically, such a method of the present invention comprises the steps of:
(i) detecting a marker protein in an animal having arteriosclerosis, which has been treated with a test therapeutic agent or by a test therapeutic method; and
(ii) evaluating the effectiveness of the test therapeutic agent or therapeutic method against arteriosclerosis based on the result of (i).

According to the method of the present invention, a marker protein is detected in an animal with arteriosclerosis, that is, an animal developing arteriosclerosis or an animal at a risk of arteriosclerosis. Preferably, before treatment with a test therapeutic agent or by a test therapeutic method, a marker protein is detected in an animal with arteriosclerosis, and then the disease stage of the atherosclerotic lesion is confirmed before treatment. After treatment of an animal with arteriosclerosis using a test therapeutic agent or by a test therapeutic method, a marker protein is detected in the animal at an appropriate time. For example, detection is performed immediately after treatment, 30 minutes after, 1 hour after, 3 hours after, 5 hours after, 10 hours after, 15 hours after, 20 hours after, 24 hours (1 day) after, 2 to 10 days after, 10 to 20 days after, 20 to 30 days after, or 1 to 6 months after treatment. Detection of a marker protein(s) and evaluation of atherosclerotic lesions can be performed in a manner similar to the above.

Subject animals in the present invention may be humans with arteriosclerotic lesions, arterial disease model animals, or preferably arteriosclerosis model experimental animals (e.g., mice, rats, and rabbits), for example. In general, after confirmation of the effectiveness of a test therapeutic agent or a test therapeutic method in a model animal, effectiveness can be evaluated in humans by clinical trials, for example.

Types of test therapeutic agent or test therapeutic method for evaluation or screening are not particularly limited. Examples of test therapeutic agents or test therapeutic methods include arbitrary material factors, specifically, naturally occurring molecules such as amino acid, peptide, oligo peptide, polypeptide, protein, nucleic acid, lipid, carbohydrate (e.g., sugar), steroid, glycopeptide, glycoprotein, and proteoglycan; synthetic analogs or derivatives of naturally occurring molecules such as peptide mimic or nucleic acid molecule (e.g., aptamer, antisense nucleic acid, and double-stranded RNA (RNAi)); molecules that do not occur naturally such as low-molecular-weight organic compound (e.g., inorganic and organic compound libraries, or combinatorial library); and mixtures thereof. Furthermore, a test therapeutic agent or a test therapeutic method may be a single substance, a complex composed of a plurality of substances, a food, a feed, or the like. Moreover, test therapeutic agents or test therapeutic methods may be, in addition to the above material factors, radiation, ultraviolet radiation, and the like.

Treatment of an animal using a test therapeutic agent or a test therapeutic method differs depending on the type of therapeutic agent or therapeutic method, and can be easily determined by persons skilled in the art. For example, persons skilled in the art can appropriately determine administration conditions such as the dosage, the dosage period, and the route of administration of a test therapeutic agent.

Furthermore, the effectiveness of a test therapeutic agent or a test therapeutic method can be examined under several conditions. Examples of such conditions include the time or the period of treatment with the test therapeutic agent or by the test therapeutic method, the amount thereof (high or low), and frequency. For example, a dilution series of a test therapeutic agent is prepared, so that a plurality of doses can be determined.

Furthermore, when the additive effects, synergistic effects, and the like of a plurality of test therapeutic agents or test therapeutic methods are examined, the therapeutic agents or therapeutic methods may be used in combination.

The amount and/or the location of a marker protein(s) in an animal after treatment with a test therapeutic agent or by a test therapeutic method is compared with the amount and/or the location of the same before treatment, so as to allow evaluation of whether or not the test therapeutic agent or the test therapeutic method is effective for improvement of atherosclerotic lesions (instability thereof) (e.g., improvement from the intermediate stage to the early intermediate stage or the initial stage), or for stopping or slowing down the progression of atherosclerotic lesions (instability thereof) (e.g., the disease progression from the intermediate stage to the late stage is stopped, unlike a case in which no treatment has been performed).

As described above, according to the method for evaluating the effectiveness of a therapeutic agent or a therapeutic method for atherosclerotic lesions (instability thereof) according to the present invention, a therapeutic agent or a therapeutic method for treating or preventing arteriosclerosis can be found, and then the effectiveness of the therapeutic agent or the therapeutic method can be confirmed. In the case of atherosclerotic lesions (instablility thereof) at the early stage in particular (the initial stage and the early intermediate stage), no sign indicating the disease can be detected. If a subject is evaluated as having arteriosclerosis at the initial stage or the early intermediate stage and some treatment is performed for the subject, it is difficult to evaluate the effectiveness of the treatment. Therefore, the method of the present invention is particularly effective for identifying a therapeutic agent or a therapeutic method effective for treatment of arteriosclerosis at the early stage.

In a manner similar to the above method, the effects of a substance or a factor on arteriosclerosis can also be determined, and thus a substance or a factor that causes the progression of atherosclerotic lesions (instability thereof) can be identified.

EXAMPLES

The present invention is hereinafter illustrated in greater detail with reference to the following examples. The examples are provided merely for the explanation of the present invention and are not intended to limit or restrict the scope of the present invention disclosed in the present application. It is apparently understood that various changes and modifications to the present invention can be made based on the concept of the present invention described herein.

Example 1

ApoE-deficient mice (ApoED; B6•KOR/StmS1c-Apoesh1), which were deficient in the lipid metabolism-related ApoE protein, were used as atherosclerosis models (Matsushima, Y. et al., J. Atheroscler. Thromb. 8: 71-79, 2001; Japan SLC, Inc.). Administration of a high-fat diet accelerates lesion progression in ApoED mice. In addition, lesion progression is accelerated depending on age in weeks. In 12-week-old mice, lesion progression is observed to such an extent that arterial intimal thickening and lipid accumulation are observed (stage 1). In 18-week-old mice, lipid accumulation results in foam cell formation (stage 2). In 25-week-old mice, many forms of unstable atherosclerotic plaque are widely observed in arteries (stage 3), and this corresponds to the most dangerous stage in the atherosclerosis process. In 35-week-old mice, many stable lesions that are highly fibrotic and calcified are observed (stage 4).

Therefore, for this example, arterial tissue was collected from 12, 18, 25, and 35-week-old wild-type mice (WT; C57BL/6) and ApoED mice (male and female mice: 5 animals each). WT and ApoED mouse arterial tissue samples were crushed in liquid nitrogen and then solubilized with a solubilization solution (9.5 M urea, 2% sulfuric acid-3-[(3-cholamidopropyl)dimethylammonio]-1-propane (CHAPS), 65 mM dithiothreitol (DTT), 40 mM Tris HCl, pH 8.3). After 20 minutes of centrifugation at 12,000 rpm and 4° C., the supernatants were recovered, acetone precipitation was performed with the addition of ice-cold acetone, and thus the protein components were concentrated. Precipitates subjected to vacuum drying were solubilized again in a re-solubilization solution (0.2% sodium dodecyl sulfate (SDS), 50 mM Tris-HCl, pH 8.5). Protein concentrations were measured and then the resultants were subjected to isotopic labeling.

The protein fractions (1 mg each) extracted from arterial tissues were adjusted in a manner such that each sample contained 6M urea, 0.05% SDS, 50 mM Tris (pH 8.5), 5 mM ethylenediamine tetraacetic acid (EDTA), and 10 mM tri-n-butyl phosphate (TBP) (final concentrations) in a total volume of 800 µl, followed by degeneration treatment at 37° C. for 30 minutes. A "Light labeling reagent" and a "Heavy labeling reagent," each of which had been dissolved with acetonitrile (200 µl), were added to a WT mouse sample and an ApoED mouse sample, respectively, followed by a labeling reaction at 37° C. for 2 hours. 800 µl of 10 mM Tris buffer (pH 8.0) was added to each sample for pH adjustment. A trypsin solution (Trypsin, TPCK Treated; Cat. No. 4352157; Applied Biosystems) (160 µl) adjusted to 125 µg/ml was added thereto. Then, both types of samples were mixed in equivalent volumes, followed by a trypsin digestion reaction at 37° C. for 16 hours. Further, peptide fragments obtained by trypsin treatment were introduced into an SCX column (poly Sulfoethyl A; 4.6×100 mm; PolyLC Inc.), followed by separation of the eluate into 25 fractions. Separation was carried out with the use of an eluent A [10 mM $KH_2PO_4$ (pH 2.8), 25% acetonitrile (ACN)] and an eluent B [10 mM $KH_2PO_4$ (pH 2.8), 25% ACN, 0.5 M KCl] with a linear gradient (% B: 10 minutes—0%, 70 minutes—20%, 85 minutes—50%, 90 minutes—60%, 95 minutes—60%, and 100 minutes—100%). Each fraction was subjected to vacuum concentration so as to result in a volume that was approximately one-fourth (¼) the initial volume. Then, desalting with a desalting column (CAPCELL C18 MG; 2.0×10 mm; Shiseido) and vacuum drying were performed. An eluent A (2% ACN, 0.05% trifluoroacetic acid (TFA)) and an eluent B (80% ACN, 0.05% TFA) were used for desalting.

Each SCX fraction was analyzed using a mass spectrometry apparatus and an accompanying LC system device (NanoFrontier LD; Hitachi High-Technologies Corporation). Each obtained sample was dissolved in a buffer A (water: 98%; ACN: 2%; formic acid: 0.1%) (4 µl to 10 µl). One microliter of each obtained solution was applied to the apparatus. A MonoCap for Fast-flow (50 µm φ×150 mm; C18; GL Sciences) was used as a sample separation column in the LC system. Analysis was carried out with a linear gradient of buffer A and buffer B (water: 2%; ACN: 98%; formic acid: 0.1%) at a flow rate of 200 nL/min, provided that the buffer B concentration reached 2% to 30% in 120 minutes. A Monolith Trap (50 µm φ×150 mm; Cat. No. C18-50-150; Hitachi High-Technologies Corporation) was used as a trap column in the apparatus. A quartz spray chip (Picotip; outer diameter: 360 µm; inner diameter: 50 µm; tip inner diameter: 10 µm; New Objective) was used as a column tip. Electrospray ionization mass spectrometry was performed in the positive ion mode. Samples obtained from 25 fractions were subjected twice to IBA (information based acquisition) analysis. IBA is a technique involving storing target information (m/z, charge number, retention time) obtained by the first analysis in a database within an apparatus, and analyzing ions that do not correspond to the target information in the second analysis. It was expected that weak ions would be analyzed with the use of such technique so as to increase the number of identified proteins. The following are additional apparatus conditions: Curtain Gas Flow: 0.7 L/min; Spray potential: 1700 V; Detector potential: 2200 V; Isolation Time: 5 ms; Isolation Width: 10 Da; and CID Time: 10 ms. The measurement data were processed using software that had been developed for ICAT comparative quantification. Thus, comparative analysis data for two groups (the WT mouse group and the ApoED mouse group) were obtained.

As a result, at least 568 proteins were confirmed to express in all 4 types (age in weeks). Proteins, the expression levels of which tended to increase or decrease stepwise in arterial tissue at the age of 12 weeks or later, were classified into the following four types of pattern. The expression level ratio for each protein was plotted against lesion progression stages (FIG. 1 to FIG. 4). Three proteins were found for which amounts thereof in 12-week-old or older ApoE-deficient mice increased to twice or more the amounts in 12-week-old or older WT (wild-type) mice (pattern 1, FIG. 1). Twelve proteins were found for which amounts thereof exhibited no significant difference until the age of 12 weeks, while the amounts thereof in 18-week-old or older ApoE-deficient mice increased to twice or more the amounts in 18-week-old or older wild-type mice (pattern 2, FIG. 2). Fourteen proteins were found for which amounts exhibited no significant difference until the age of 18 weeks, while the amounts thereof in 25-week-old or older ApoE-deficient mice increased to twice or more the amounts in 25-week-old or older wild type mice (pattern 3, FIG. 3). Seven proteins were found for which amounts exhibited no significant difference until the age of 25 weeks, while the amounts thereof in 35 week-old ApoE-deficient mice increased to twice or more the amounts in 35 week-old wild-type mice (pattern 4, FIG. 4). From these protein groups, marker proteins related to the progression of atherosclerotic lesions were extracted according to the following criteria.

From among proteins belonging to the pattern 3, four proteins characterized in that: (i) the ratio of the amounts thereof in ApoE-deficient mice divided by the amounts thereof in wild-type mice (herein after referred to as "the expression level ratio") at the age of 25 weeks was at least 3; and (ii) the expression level ratio at the age of 25 weeks was at least twice as large as the expression level ratio at the age of 18 weeks, were selected as markers indicating the risk of plaque rupture at the intermediate stage (Table 1).

From among proteins belonging to patterns 1 and 2, seven proteins were selected as markers indicating the progression of plaques from the initial to the intermediate stages (Table 2). These proteins were characterized in that: (i) the expression level ratio at the age of 18 weeks was at least 2; (ii) the expression level ratio at the age of 18 weeks was at least 1.3 times as large as the expression level ratio at the age of 12 weeks; (iii) the expression level ratio at the age of 25 weeks was at least 4; and (iv) the expression level ratio at the age of 25 weeks was at least 1.3 times as large as the expression level ratio at the age of 18 weeks.

From among proteins belonging to the patterns 2 and 4, three proteins characterized in that: (i) the expression level ratio at the age of 35 weeks was at least 4; and (ii) the expression level ratio at the age of 35 weeks was at least twice as large as the expression level ratio at the age of 25 weeks, were selected as markers indicating stabilization of plaques at the late stage (Table 3).

In addition, from among proteins belonging to the patterns 1 to 4, 22 proteins not selected in Table 1 to Table 3 are categorized into another marker group relating to the progression of atherosclerotic lesions, as listed in Table 4.

Example 2

Arterial tissues were excised from five 12-week-old ApoE knockout mice (female) from different lines (ApoEKO; B6.129P2-ApoetmlUnc/J) fed with a normal diet, and then protein fractions (pool) were prepared in a manner similar to that in Example 1. The ApoEKO line differing from the ApoED line described in Example 1 (Piedrahita, J A. et al., Proc. Natl. Acad. Sci. U.S.A., 89: 4471-4475, 1992; Charles River Laboratories, Japan Inc.) were confirmed in advance in a preliminary study to have no lesion formed in arteries (data not shown). The lipid concentrations in blood of a subject were: total cholesterol of 539 mg/dl; triglyceride of 49 mg/dl; LDL cholesterol of 404 mg/dl; and HDL cholesterol of 143 mg/dl. Thus, the progression of arteriosclerosis was suspected. Hence, the ratios of the expression levels of proteins contained in tissue samples were exhaustively analyzed by the method of Example 1 (that had been partially modified) using an arterial tissue obtained from a wild-type mouse (WT; C57BL/6) at the same age in weeks as a standard level. The partial modification in the method of Example 1 is that the number of SCX fractions was 7 instead of 25 for simplifying experimental procedures.

As a result, 247 proteins were identified, which were the same as those included in the proteins identified in Example 1. Of these proteins, a protein group, the ratio of the amounts of which in ApoE-deficient mice divided by those in wild-type mice was at least 2 in Example 1, was examined for behavior. Three proteins (C4BPA_MOUSE, MUCM_MOUSE, PROP_MOUSE), the amounts of which in 12-week-old or older ApoE-deficient mice increased to twice or more the amounts in 12-week-old or older wild-type mice in Example 1, were not identified in this measurement. Of the proteins (total of 32 proteins), the amounts of which in 18-week-old or older ApoE-deficient mice increased to twice or more the amounts in 18-week-old or older wild-type mice in Example 1, eleven proteins could be identified in this measurement. However, the ratio of the amount of each of these eleven proteins in ApoE-deficient mice divided by the same in wild-type mice was always 1.35 or less. Therefore, the mice subjected to this measurement were most likely at the progression stage of arteriosclerosis corresponding to the age of 12 weeks (initial lesion). Thus, the effectiveness of the present invention was demonstrated.

Example 3

Ten typical proteins were selected from the candidate marker protein group that exhibited variations in Example 1 (characteristic in ApoE-deficient mice) in the amounts thereof in arterial tissues. The expression of the proteins in atherosclerotic lesion sites was confirmed by immunohistochemical staining of lesion sites (plaque formation sites) in arterial tissues of ApoE-deficient mice at different ages in weeks.

Each aortic sample subjected to 10% formalin fixation was coronally excised at the aortic arch, and then a paraffin embedded block was prepared. Subsequently, it was sliced to a thickness of 3 μm, and then the slices were subjected to immunohistochemical staining according to a conventional method using hematoxylin•eosin (H&E) staining and antibodies. Primary antibodies used for immunohistochemical staining are as follows.
Anti-properdin antibody (50-fold dilution, sc68367; Santa Cruz),
Anti-CD5 antigen-like protein antibody (100-fold dilution, ab45408; Abcam),
Anti-fibronectin antibody (50-fold dilution, sc59826; Santa Cruz),
Anti-fibromodulin antibody (50-fold dilution, sc33772; Santa Cruz),
Anti-thrombospondin-4 antibody (50-fold dilution, sc68367; Santa Cruz),
Anti-plastin-2 antibody (50-fold dilution, 13025-1-AP; Proteintech),
Anti-ADAMTS-like protein 4 antibody (50-fold dilution, 15304-1-AP; Proteintech),
Anti-matrix metalloproteinase-2 antibody (50-fold dilution, BS1236; Bioworld Technology),
Anti-tenascin antibody (50-fold dilution, 3118-1; Epitomics),
Anti-cartilage oligomeric matrix protein antibody (50-fold dilution, PC-140; Kamiya Biomedical Company).

After reaction with a biotin-labeled secondary antibody, signals were visualized with the addition of diaminobenzidine (DAB). Stained specimens were observed under a microscope (Biozero, BZ-8000; KEYENCE CORPORATION) and then the thus obtained images were stored as digital data.

Figure 6:
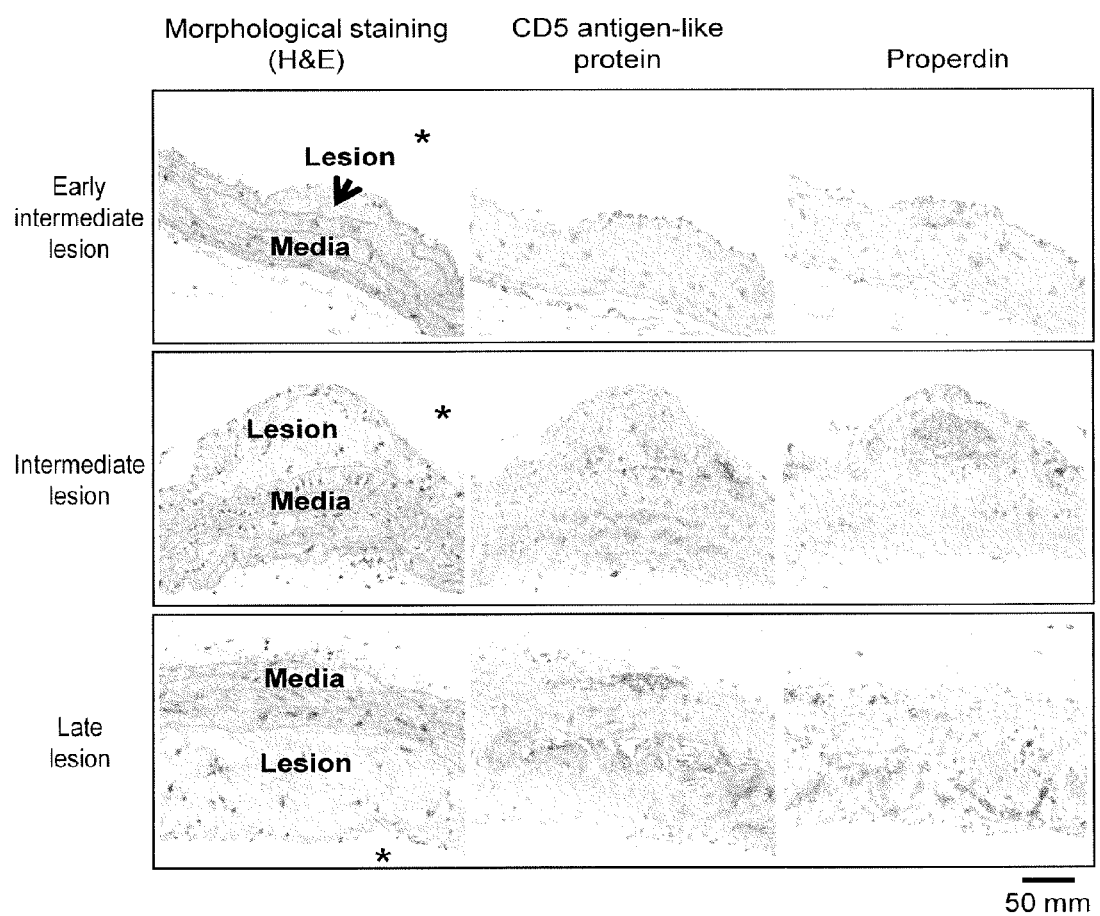
FIG. 6 shows images showing the expression of markers (CD5 antigen-like protein and properdin) in atherosclerotic lesions.
Figure 7:
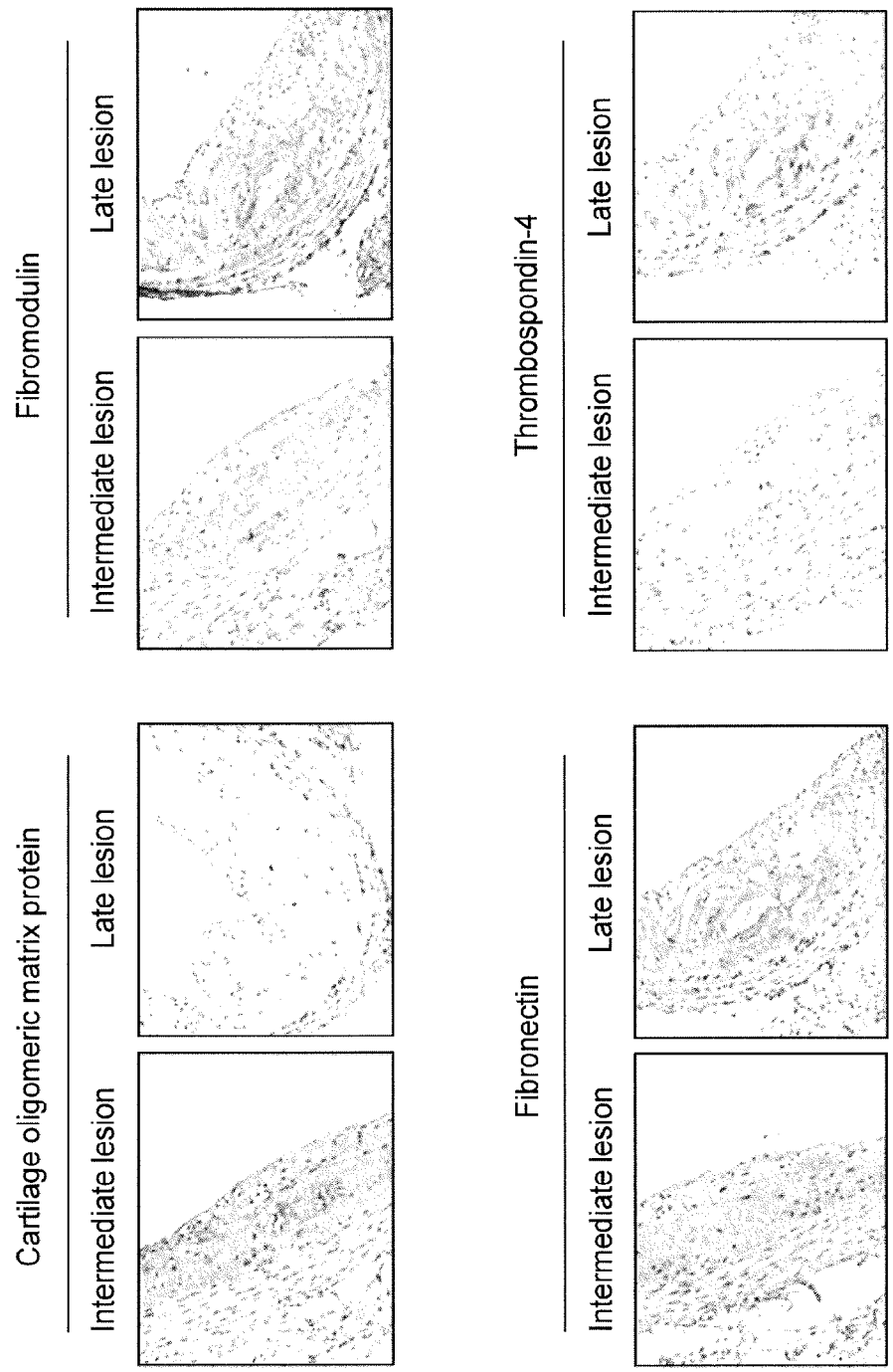
FIG. 7 shows images showing the expression of markers (cartilage oligomeric matrix protein, fibromodulin, fibronectin, and thrombospondin-4) in atherosclerotic lesions.

FIG. 6 shows the results of immunohistochemical staining using the anti-CD5 antigen-like protein antibody and the anti-properdin antibody. Moreover, FIG. 7 shows the results of immunohistochemical staining using the anti-cartilage oligomeric matrix protein antibody, the anti-fibromodulin antibody, the anti-fibronectin antibody, and the anti-thrombospondin-4 antibody. Furthermore, FIG. 8 shows the results of immunohistochemical staining using the anti-plastin-2 antibody and the anti-tenascin antibody.

As shown in these figures, as a result of immunohistochemical staining using the anti-properdin antibody, the anti-CD5 antigen-like protein antibody, the anti-plastin-2 antibody, and the anti-tenascin antibody, high signals were detected for the lesion sites at particularly the intermediate stage, the expression of the target protein group to be recognized by each antibody in lesions was confirmed, and thus the results obtained by mass spectroscopy in Example 1 were supported (FIG. 6 and FIG. 8). Also, as a result of immunohistochemical staining using the anti-fibromodulin antibody, the anti-fibronectin antibody, and the anti-thrombospondin-4 antibody, high signals were detected for lesion sites at the intermediate stage in particular and the late stage, the expression of the target protein group to be recognized by each antibody in the lesions was confirmed, and thus the results of Example 1 were supported (FIG. 7). Also, as a result of immunohistochemical staining using the anti-cartilage oligomeric matrix protein antibody, higher signals were detected for lesion sites at the intermediate stage than the same at the late stage, and the expression of the target protein in lesions was confirmed (FIG. 7). Since 35-week-old mouse arterial tissues contain intermediate stage lesions in addition to late stage lesions, the result that the cartilage oligomeric matrix protein exhibited strong expression in the intermediate stage lesions is consistent with the result of mass spectroscopy in Example 1. Moreover, as a result of immunohistochemical staining using the anti-matrix metalloproteinase-2 antibody, high signals were detected for lesion sites at the late stage in particular, the expression of the target protein to be recognized by the antibody in the lesions was confirmed, and thus the results of Example 1 were supported. As a result of immunohistochemical staining using the anti-ADAMTS-like protein 4 antibody, an increase in signal intensity was observed with the progression of stages. The expression of target proteins to be recognized by these antibodies in lesions was confirmed, and thus the results of Example 1 were supported.

As described above, it was confirmed that the ratio of the amounts of the proteins in ApoE-deficient mice to those in wild-type mice had a high correlation with the amounts of the proteins in atherosclerotic lesions (FIG. 6 to FIG. 8).

Example 4

WHHL arteriosclerosis model rabbits formed atherosclerotic lesions, the progression degree of which differs depending on age in months. In this example, 7-week-old and 13-week-old WHHL rabbits (male, Kitayama Labs) were used. A $^{99m}$technetium-labeled anti-properdin antibody and a $^{125}$iodine-labeled anti-CD5L antibody were mixed, the mixture was administered (under anesthesia) into the marginal vein of the ear of each rabbit, and then the ways in which signals from both antibodies were accumulated in lesions were examined. Signal accumulation 6 hours after administration was visualized using an animal SPECT device (R1; Hitach, Ltd.).

Only the anti-properdin antibody-derived signals were detected in 7-week-old WHHL rabbits; however, in the case of 13-week-old WHHL rabbits, anti-properdin antibody-derived signals and anti-CD5L antibody-derived signals were detected mainly in the thoracic aortic arch. On the other hand, no signals from either antibody were ever detected in the case of 13-week-old wild-type rabbits (Japanese white; Kitayama Labs).

All publications, patents, and patent applications cited herein are incorporated herein by reference in their entirety

INDUSTRIAL APPLICABILITY

According to the present invention, technology for evaluation of the presence or the absence of the onset of arteriosclerosis and the progression thereof is provided. The presence or the absence, the state or the progression degree, and the location of arteriosclerosis can be conveniently determined with high accuracy according to the present invention. Furthermore, according to the present invention, a method for screening for a medicine useful for prevention and/or treatment of arteriosclerosis is provided. The present invention is useful in the field of diagnosis, prevention, and/or treatment of arteriosclerosis.

The invention claimed is:

1. An apparatus for evaluating an atherosclerotic lesion at the initial or the intermediate stage, comprising:
   (i) a means of detecting plastin-2 in a subject;
   (ii) a means of detecting at least one type of protein selected from each of group (a), (b), (c), and (d) from among proteins shown in the following groups (a) to (d), in a subject:
      (a) cartilage oligomeric matrix protein, fibromodulin, fibronectin, and thrombospondin-4;
      (b) tenascin, CD5 antigen-like protein, properdin, Cb4-binding protein, fibrinogen beta chain, and fibrinogen gamma chain;
      (c) vitronectin, matrix metalloproteinase-2, and thrombospondin-1; and
      (d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4; and
   (iii) a means of evaluating the atherosclerotic lesion at the initial or the intermediate stage in the subject based on the detection results obtained by means (i) and (ii);
   wherein the apparatus comprises at least one of the following to detect the plastin-2: positron emission tomography (PET), single photon emission computed tomography (SPECT), γ scintigraphy, autoradiography, fluorescent imaging, magnetic resonance imaging (MRI), ultrasonication, and computed tomography (CT), a biosensor, a solid-phase support to which an antibody against a marker has been immobilized, mass spectoscropy, a surface plasmon resonance sensor, and an NMR analyzer; and
   wherein the apparatus further comprises at least one of the following to evaluate the atherosclerotic lesion: an image-numeric data storage part, standard level data storage part, a data comparison part and a data analysis part for analysis of data, data output-display part, a software and a computer unit for activating a computer part.

2. The apparatus according to claim 1, further comprising:
(iv) a means of storing the standard levels of the above proteins; and
(v) a means of comparing the protein detection results in the subject with the standard levels;
wherein the apparatus comprises a protein standard level database with expression data containing pathological (arteriosclerosis) stage-specific expression data.

3. A method for evaluating the effectiveness of a therapeutic agent or a therapeutic method for an atherosclerotic lesion at the initial or the intermediate stage, comprising the steps of:
(i) detecting plastin-2 in an animal with an atherosclerotic lesion before treatment using the test therapeutic agent or the test therapeutic method;
(ii) detecting plastin-2 in an animal with an atherosclerotic lesion at the initial or the intermediate stage treated by a test therapeutic agent or a test therapeutic method; and
(iii) evaluating the effectiveness of the test therapeutic agent or the test therapeutic method on the atherosclerotic lesion at the initial or the intermediate stage based on the results of (i) and (ii).

4. A method for evaluating the effectiveness of a therapeutic agent or a therapeutic method for an atherosclerotic lesion at a certain stage, comprising the steps of:
(i) detecting plastin-2 and at least one type of protein selected from at least each of group (a), (b), (c) and (d) from among proteins shown in the following groups (a) to (d) in an animal with an atherosclerotic lesion treated by a test therapeutic agent or a test therapeutic method:
(a) thrombospondin-4, fibromodulin, fibronectin, and cartilage oligomeric matrix protein;
(b) tenascin, CD5 antigen-like protein, properdin, Cb4-binding protein, fibrinogen beta chain, and fibrinogen gamma chain;
(c) vitronectin, matrix metalloproteinase-2, and thrombospondin-1; and
(d) membrane-bound form immunoglobulin mu chain C region, receptor-type tyrosine protein phosphatase C, immunoglobulin gamma-2B chain-C region, immunoglobulin J chain, immunoglobulin kappa chain C region, vascular cell adhesion protein 1, alpha-2-macroglobulin, ADAMTS-like protein 4, cathepsin B, carboxy peptidase-B2, complement factor-H, clusterin, collagen alpha-1 (XIV) chain, epidermal fatty acid-binding protein, mannose-binding lectin-associated serine protease-2, prothrombin, complement factor B, inter-alpha-trypsin inhibitor-heavy chain-H1, myosin-9, vitamin K-dependent factor S, metalloproteinase inhibitor 3, and tropomyosin alpha 4; and
(ii) evaluating the effectiveness of the test therapeutic agent or the test therapeutic method on the atherosclerotic lesion at a certain stage based on the results of (i).

5. The method according to claim 3, wherein an animal having an atherosclerotic lesion is an arterial disease animal model.

* * * * *